US007875444B2

(12) United States Patent
Yang et al.

(10) Patent No.: US 7,875,444 B2
(45) Date of Patent: *Jan. 25, 2011

(54) LIGNIN BLOCKERS AND USES THEREOF

(75) Inventors: Bin Yang, West Lebanon, NH (US); Charles E. Wyman, Norwich, VT (US)

(73) Assignee: The Trustees of Dartmouth College, Hanover, NH (US)

( * ) Notice: Subject to any disclaimer, the term of this patent is extended or adjusted under 35 U.S.C. 154(b) by 151 days.

This patent is subject to a terminal disclaimer.

(21) Appl. No.: 11/229,817

(22) Filed: Sep. 19, 2005

(65) Prior Publication Data

US 2006/0088922 A1    Apr. 27, 2006

Related U.S. Application Data

(63) Continuation-in-part of application No. 10/391,740, filed as application No. PCT/US2004/008730 on Mar. 9, 2004, now Pat. No. 7,604,967.

(51) Int. Cl.
*C12P 7/06* (2006.01)
*C12P 7/08* (2006.01)
*C12P 7/10* (2006.01)
*C12P 19/14* (2006.01)
*C12P 21/06* (2006.01)
*C07K 14/415* (2006.01)
*C07K 14/765* (2006.01)

(52) U.S. Cl. .................. 435/161; 435/68.1; 435/99; 435/163; 435/165; 530/363; 530/370; 530/378

(58) Field of Classification Search .................. None
See application file for complete search history.

(56) References Cited

U.S. PATENT DOCUMENTS

| | | |
|---|---|---|
| 4,009,075 A | 2/1977 | Hoge |
| 4,167,587 A * | 9/1979 | Danforth .................. 426/250 |
| 4,237,226 A | 12/1980 | Grethlein |
| 4,556,430 A | 12/1985 | Converse et al. |
| 4,668,340 A | 5/1987 | Sherman |
| 4,708,746 A | 11/1987 | Hinger |
| 4,746,401 A | 5/1988 | Roberts et al. |
| 4,861,721 A | 8/1989 | Waterbury et al. |
| 5,125,977 A | 6/1992 | Grohmann et al. |
| 5,258,293 A | 11/1993 | Lynd et al. |
| 5,424,417 A | 6/1995 | Torget et al. |
| 5,503,996 A | 4/1996 | Torget et al. |
| 5,529,663 A | 6/1996 | Springer |
| 5,536,325 A | 7/1996 | Brink |
| 5,688,674 A | 11/1997 | Choi et al. |
| 5,705,369 A | 1/1998 | Torget et al. |
| 5,837,506 A | 11/1998 | Lynd et al. |
| 6,022,419 A | 2/2000 | Torget et al. |
| 6,063,204 A | 5/2000 | Hester et al. |
| 6,159,510 A | 12/2000 | Lizak |
| 6,252,109 B1 * | 6/2001 | Rousu et al. .................. 562/513 |
| 2006/0008885 A1 * | 1/2006 | Wahnon et al. .................. 435/105 |

FOREIGN PATENT DOCUMENTS

| | | |
|---|---|---|
| EP | 0268575 A2 | 5/1988 |
| GB | 24738 A | 0/1914 |
| WO | WO 94/29474 A | 12/1994 |

OTHER PUBLICATIONS

Baker, J.O., et al. "Investigation of the cell-wall loosening protein expansin as a possible additive in the enzymatic saccharification of lignocellulosic biomass" Applied Biochemistry and Biotechnology, 2000, 84-86 (1-9), pp. 217-224.*
Eriksson, T et al. "Mechanism of surfactant effect in enzymatic hydrolysis of lignocellulose" Enzyme Microbial Technology. 2002, 31(3), 353-364.*
Ingram, L. et al "Fuel Ethanol Production from Lignocellulose Using Genetically Engineered Bacteria" ACS Symposium Series: Fuels and biomass 1997, 666, pp. 57-73. (CAS Abstract only).*
Kadam, K.L. and Schmidt, S.L. "Evaluation of *Candida acidothermophilum* in Ethanol Production from Lignocellulosic Biomass" Applied Microbiology and Biotechnology. 2000, vol. 84-86, pp. 217-223.(CAS Abstract only).*
Gracheck, S.J.; Rivers, D.B.; Woodford, L.C.; Giddings, K.E.; Emert, G.H. "Pre-treatment of Lignocellulosics to Support Cellulase Production Using *Trichoderma reesei* QM9414" Biotechnology and Bioengineering Symposium. 1982, 666, pp. 47-66.(CAS Abstract only).*
Ingram, L. et al "Fuel Ethanol Production from Lignocellulose Using Genetically Engineered Bacteria" ACS Symposium Series: Fuels and biomass 1997, 666, pp. 57-73.*
Kadam, K.L. and Schmidt, S.L. "Evaluation of *Candida acidothermophilum* in Ethanol Production from Lignocellulosic Biomass" Applied Microbiology and Biotechnology. 1997, 48(6), pp. 709-713.*
Gracheck, S.J.; Rivers, D.B.; Woodford, L.C.; Giddings, K.E.; Emert, G.H. "Pre-treatment of Lignocellulosics to Support Cellulase Production Using *Trichoderma reesei* QM9414" Biotechnology and Bioengineering Symposium. 1982, 666, pp. 47-65.*

(Continued)

*Primary Examiner*—Christopher R Tate
*Assistant Examiner*—Aaron J Kosar
(74) *Attorney, Agent, or Firm*—Lathrop & Gage LLP

(57) ABSTRACT

Disclosed is a method for converting cellulose in a lignocellulosic biomass. The method provides for a lignin-blocking polypeptide and/or protein treatment of high lignin solids. The treatment enhances cellulase availability in cellulose conversion and allows for the determination of optimized pretreatment conditions. Additionally, ethanol yields from a Simultaneous Saccharification and Fermentation process are improved 5-25% by treatment with a lignin-blocking polypeptide and/or protein. Thus, a more efficient and economical method of processing lignin containing biomass materials utilizes a polypeptide/protein treatment step that effectively blocks lignin binding of cellulase.

21 Claims, 12 Drawing Sheets

OTHER PUBLICATIONS

Shi, J, et al "The Potential of Cellulosic Ethanol Production from Municipal Solid Waste: A Technical and Economic Evaluation", UCEI Energy Policy and Economics Working Paper Series, Apr. 2009, retrieved from internet <http://www.ucei.berkeley.edu/PDF/EDT_015.pdf>, 41 pages.*

Leisola, M.S.A., et al "Factors affecting lignin degradation in lignocellulose by *Phanerochaete chrysosporium*" Archives of Microbiology, 1984, 137(2), pp. 171-175.*

Shernoglazov, et al., "Adsorption of High-Purity Endo-1, 4-6-βlucanases From *Trichoderma reesei* On Components Of Lignocelluasis Materials: Cellulose, Lignin And Xylan" Enzyme Microb. Technology, vol. 10, Aug. 1988 pp. 503-507.

International Search Report and Written Opinion dated Jul. 27, 2005 issued in related PCT Patent Application Serial No. PCT/US2004/008730.

Stryer, L.; Biochemistry, Third Edition, 1988, Chapt. 8; pp. 177-184.

Wyman, Charles E., "Biomass Ethanol: Technical Progress, Opportunities, and Commercial Challenges", Annu. Rev. Energy Environ. 1999, V. 24, pp. 189-226.

Wyman, Charles E., Spindler, Diane D., and Grohmann, Karel, "Simultaneous Saccharification and Fermentation of Several Lignocellulosic Feedstocks to Fuel Ethanol", Biomass and Bioenergy, 1992, vol. 3, No. 5, pp. 301-307, Pergamon Press Ltd., Great Britain.

Wyman, Charles E., "Ethanol from Lignocellulosic Biomass: Technology, Economics, and Opportunities", Bioresource Technology 50, 1994, pp. 3-16, Elsevier Science Limited, Great Britain.

Wyman, C.E., Spindler, D.D., Grohmann, K. and Lastick S.M., "Simultaneous Saccharification and Fermentation of Cellulose with the Yeast *Brettanomyces clausenii*", Biotechnology and Bioengineering Symp. No. 17, 1986, pp. 221-238.

Wyman, Charles E., "Twenty Years of Trials, Tribulations, and Research Progress in Bioethanol Technology", Applied Biochemistry and Biotechnology, 2001, V. 91-93, pp. 5-21, The Humana Press Inc.

Wright, John D., Wyman, Charles E. and Grohmann, Karel, "Simultaneous Saccharification and Fermentation of Lignocellulose", Applied Biochem. Biotechnol.,1988, 17, pp. 75-90.

Spindler, Diane D., Wyman, Charles E., Mohagheghi, Ali, and Grohmann, Karel, "Thermotolerant Yeast for Simultaneous Saccharification and Fermentation of Cellulose to Ethanol", Applied Biochem. Biotechnol., 1988, 17, pp. 279-293.

Spindler, Diane D., Wyman, Charles E., Grohmann, Karel and Philippidis, George P., "Evaluation of the Cellobiose-Fermenting Yeast *Brettanomyces custersii* in the Simultaneous Saccharification and Fermentation of Cellulose", Biotechnology Letters, May 1992, V. 14 No. 5, pp. 403-407.

Spindler, Diane D., Wyman, Charles E., and Grohmann, Karel, "The Simultaneous Saccharification and Fermentation of Pretreated Woody Crops to Ethanol", Applied Biochemistry and Biotechnology, 1991, vol. 28/29, pp. 773-786.

Spindler, Diane D., Wyman, Charles E., Grohmann, Karel and Mohagheghi, Ali, "Simultaneous Saccharification and Fermentation of Pretreated Wheat Straw to Ethanol with Selected Yeast Strains and B-Glucosidase Supplementation", Applied Biochemistry and Biotechnology, 1989, vol. 20/21, pp. 529-540.

Spindler, Diane, Wyman, Charles and Grohmann, Karel; "Evaluation of Pretreated Herbaceous Crops for the Simultaneous Saccharification and Fermentation Process", Applied Biochemistry and Biotechnology, 1990, vol. 24/25, pp. 275-286.

Yang, Bin, Boussaid, Abdel, Mansfield, Shawn D., Gregg, David J. and Saddler, John N., "Fast and Efficient Alkaline Peroxide Treatment to Enhance the Enzymatic Digestibility of Steam-Exploded Softwood Substrates", Biotechnology and bioengineering, Mar. 20, 2002, vol. 77, No. 6, pp. 678-684.

Sewalt, V.J.H., Glasser, W.G. and Beauchemin, K.A., "Lignin Impact on Fiber Degradation. 3. Reversal of Inhibition of Enzymatic Hydrolysis by Chemical Modification of Lignin and by Additives", J. Agric. Food Chem, 1997, vol. 45, No. 5, pp. 1823-1828, American Chemical Society.

Mohagheghi, A., Tucker, M., Grohmann, K. and Wyman, C., "High Solids Simultaneous Saccharification and Fermentation of Pretreated Wheat Straw to Ethanol", Applied Biochemistry and Biotechnology, 1992, vol. 33, pp. 67-81, The Humana Press Inc.

Lu, Yanpin, Yang, Bin, Gregg, David, Saddler, John N. and Mansfield, Shawn D., "Cellulase Adsorption and an Evaluation of Enzyme Recycle During Hydrolysis of Steam-Exploded Softwood Residues", Applied Biochemistry and Biotechnology, 2002, vol. 98-100, pp. 641-654, Humana Press Inc.

Eriksson, Tony, Borjesson, Johan and Tjerneld, Folke, "Mechanism of surfactant effect in enzymatic hydrolysis of lignocellulose", Enzyme and Microbial Technology 2002, v. 31, pp. 353-364, Elsevier Science Inc.

Torget, R., Himmel, M. and Grohmann, K.; "Dilute-Acid Pretreatment of Two Short-Rotation Herbaceous Crops", Applied Biochemistry and Biotechnology, 1992, vol. 34/35, pp. 115-123, The Humana Press Inc.

Sutcliffe, Roger and Saddler, John N., "The role of Lignin in the Adsorption of Cellulases during Enzymatic Treatment of Lignocellulosic Material", Biotechnology and Bioengineering Symp. No. 17, 1986, pp. 749-762.

Wu, Michael M., Chang, Kevin, Gregg, David J., Boussaid, Abdel, Beaston, Rodger P. and Saddler, John N. "Optimization of Steam Explosion to Enhance Hemicellulose Recovery and Enzymatic Hydrolysis of Cellulose in Softwoods", Applied Biochemistry and Biotechnology, 1999, vol. 77-79, pp. 47-54, The Humana Press Inc.

Grohmann, K., Torget, R. and Himmel, M., "Dilute Acid Pretreatment of Biomass at High Solids Concentrations", Biotechnology and Bioengineering Symp. No. 17, 1986, pp. 135-151.

Chernoglazov, Vladimir M., Ermolova, Olga V. and Klyosov, Anatole A., "Adsorption of high-purify endo-1,4-β-glucanases from *Trichoderma reesei* on components of lignocellulosic materials: cellulose, lignin, and xylan", Enzyme Microb. Technol., 1988, vol. 10, August, pp. 503-507.

Boussaid, Abdel, Robinson, Jamie, Cai, Yi-Jin, Gregg, David J. and Saddler, John N., "Fermentabililty of the Hemicellulose Derived Sugars from Steam-Exploded Softwood (Douglas Fir)", Int'l Conf. Biotechnol. Pulp Pap. Ind., 7th, 1998, pp. C239-C242.

Gould, Michael J., "Alkaline Peroxide Delignification of Agricultural Residues to Enhance Enzymatic Saccharification", Biotechnology and Bioengineering, 1984, vol. XXVI, pp. 046-052, John Wiley & Sons, Inc.

Ghose, T.K., Roychoudhury, P.K. and Ghosh, P., "Simultaneous Saccharification and Fermentation (SSF) of Lignocellulosics to Ethanol Under Vacuum Cycling and Step Feeding", Biotechnology and Bioengineering, 1984, vol. XXVI, pp. 377-381, John Wiley & Sons, Inc.

Overend, R.P. and Chornet, E., "Fractionation of Lignocellulosics by Steam-Aqueous Pretreatments", Philosophical Transactions of the Royal Society of London, Series A, Mathematical and Physical Sciences, Apr. 30, 1987, vol. 321, issue 1561, Technology in the 1990s: Utilization of Lignocellulosic Wastes, pp. 523-536, The Royal Society.

Schwald, W., Smaridg, T., Chan, M., Breuil, C. and Saddler, J.N., "The influence of $SO_2$ impregnation and fractionation on product recovery and enzymic hydrolysis of steam-treated sprucewood", 1989, pp. 231-242 Goughlan, M.P., Elsivier, N.Y.

Kadla, John F., Chang, Hou-Min, and Jameel, Hasan, "The Reactions of Lignins with High Temperature Hydrogen Peroxide", Holzforschung, 1999, vol. 53, No. 3, pp. 277-284, Walter de Gruyter, Berlin-New York.

Brooks, Ronald E. and Bellamy, W. Dexter, "Bioconversion of Plant Biomass to Ethanol", Proc. Annu. Fuels Biomass Symp., $2^{nd}$, 1978, pp. P-513-P-536.

Boussaid, A., Jarvis, J., Gregg, D.J. and Saddler, J.N., Optimization of Hemicellulose Sugar Recovery from a Steam-Exploded Softwood (Douglas Fir), Proc. Biomass Conf. of the Americas, $23^{rd}$, Montreal, Aug. 24-29, 1997, pp. 873-881.

U.S. Appl. No. 10/391,740, Image File Wrapper (without cited references) through Oct. 29, 2007, 218 pages.

Notice of Allowance issued in related U.S. Appl. No. 10/391,740, mailed Dec. 31, 2008, 4 pages.

* cited by examiner

LIGNIN BLOCKERS AND USES THEREOF

CROSS REFERENCE TO RELATED APPLICATION

This application is a Continuation-In-Part of related applications Ser. No. 10/391,740, filed Mar. 19, 2003 now U.S. Pat. No. 7,604,967, and PCT/US2004/008730, filed Mar. 9, 2004, which are incorporated herein by reference.

GOVERNMENT INTERESTS

The United States Government may have certain rights in the present invention as research relevant to its development was finded by United States Department of Energy (DOE) contract numbers DE FC36-00GO010589 and DE FC36-01GO11075 and by the National Institute of Standards and Technology (NIST) contract number 60NANB1D0064.

BACKGROUND

1. Field of the Invention

The present invention pertains to the field of biomass processing to produce fuels, chemicals and other useful products and, more specifically, to saccharifying lignocellulosic biomass materials to produce sugars for conversion to ethanol and other products with enhanced Glycosidases, such as cellulase and xylanase efficacy through selective binding or blocking of the lignin component. Use of a protein wash enhances bioconversion efficiency by increasing the availability of cellulase and other enzymes to cellulose.

2. Description of the Related Art

Cellulosic biomass is useful for generating ethanol. Such materials specifically known as lignocellulosic materials, or biomass, (e.g. wood and solid wastes), have been used as source material to generate carbohydrates, which in turn may be used to produce ethanol, as well as other products.

Lignocellulosic biomass is a complex structure of cellulose fibers wrapped in a lignin and hemicellulose sheath. The ratio of the three components varies depending on the type of biomass. Typical ratios are as follows:

TABLE 1

|  | SOFT-WOODS | CORN COBS | RDF* | CORN STOVER |
|---|---|---|---|---|
| CELLULOSE | 42% | 40% | 52% | 37% |
| HEMICELLULOSE | 25% | 36% | 26% | 22% |
| LIGNIN | 28% | 13% | 20% | 17% |
| OTHER | 5% | 11% | 2% | 24% |

*RDF—REFUSE DERIVED FUEL FROM MUNICIPAL WASTE SYSTEMS

Table 1 is only an approximation. For example, wood differs in composition, depending on the particular type of wood, where softwoods (gymnosperms) generally have more glucomannans and less glucuronoxylans than do hardwoods.

Cellulose is a polymer of D-glucose monomer with $\beta$-1-4-linkages between each monomer forming chains of about 500 to 10,000 D-glucose units. Hemicellulose is a polymer of sugars, primarily D-xylose with other pentoses and some hexoses, also with $\beta$-1-4-linkages. Lignin is a complex random polyphenolic polymer. Lignocellulose biomass represents an inexpensive and readily available substrate for the preparation of sugars. These sugars may be used alone, fermented to produce alcohols and industrial chemicals, or chemically converted to other compounds.

Ethanol is one of the alcohols that may be produced using carbohydrate derived from a lignocellulosic biomass, and has a number of industrial and fuel uses. Of particular interest is the use of ethanol as a gasoline additive that boosts octane, reduces pollution, and partially replaces gasoline in fuel mixtures. Ethanol-blended gasoline formulations are well-known commercial products commonly called "gasohol". It has been proposed to eliminate gasoline almost completely from the fuel and to burn ethanol in high concentrations.

Conversion of cellulose biomass into renewable fuels and chemicals often involves chemical and/or enzymatic treatment of the biomass with cellulase or other enzymes. In particular, cellulase enzymes hydrolyze cellulose to D-glucose, which is a simple sugar. In high lignin content lignocellulosic biomass, high doses of cellulase are needed to degrade the cellulose with high yields because the lignin binds preferentially with the cellulase, thereby reducing access of cellulase to cellulose. Consequently, when processing high lignin content biomass materials, less cellulase is available to degrade cellulose because the lignin coating of the cellulose fibers scavenges cellulase. Thus, the effectiveness of the process for digesting cellulose is reduced.

Bioconversion of cellulose biomass to ethanol has been studied since the 1940's. However, the cellulose-to-ethanol process is not yet economical compared to producing petroleum products by existing technology. Enzymatic hydrolysis is a fairly slow process. The costs of cellulases are high, and the required amount of cellulases is also high, which increases processing costs. Reduction in the amount of cellulase needed to obtain a satisfactory sugar yield can have a significant impact on process economics. Therefore, improving the efficiency of enzyme use is a major need in the bioconversion process.

The mechanism of hydrolysis and the relationship between the structure and function of various cellulases have been extensively studied. Several factors are thought to influence enzymatic hydrolysis of cellulose. These factors include lignin content, hemicellulose content, acetyl content, surface area of cellulose and cellulose crystallinity. It is generally understood that the lignin present in complex substrates, such as steam-exploded wood, especially softwoods, has a negative effect on cellulase activity. The exact reasons are poorly understood because the complexity of biomass is such that reducing one barrier to digestion can enhance or disguise the importance of others. For example, cellulose hydrolysis has been shown to improve with increasing lignin removal, although differences are reported in the degree of lignin removal that is needed, as well as the physical form of the lignin.

A variety of factors may be associated with the deleterious effects of lignin upon saccharification. The ratio of syringyl moiety to guaiacyl moiety in the lignin may affect saccharification. Although the exact role of lignin in limiting hydrolysis has been difficult to define, one probable significant limitation is the effect of lignin on fiber swelling and the resulting influence on cellulose accessibility. The removal of lignin increases accessibility of cellulose and allows more cellulase activity. This is problematic in that some lignin complexes are physically and chemically resistant to enzymatic attack. While some lignin components are water soluble, others are insoluble and may precipitate from solution. Condensed lignin has the ability to adsorb protein from aqueous solutions. Lignin removal may open more surface area for enzymatic attack and reduce the amount of cellulase that is non-specifically adsorbed on the lignocellulosic substrate. Studies involving acid pretreated softwood report a positive correlation between digestibility and the extent of delignification, but the results are complicated by the presence of hemicellulose. Some substrates require higher temperatures for hemicellulose removal to be effective; suggesting that hemicellulose is not the only additional factor impacting digestibility and other evidence does not support a role for hemicellulose in changing cellulose digestibility.

Although cellulose crystallinity is generally reasoned to impede enzymes, rates slow with increasing crystallinity in some studies, but increase in other studies. The degree of crystallinity may not significantly change over an extended hydrolysis time. Crystallinity seems less important than lignin removal and impacts saccharification rates more than yields. Several studies have focused on explaining cellulose digestibility by the accessibility of cellulose to enzymes. Correlations have been developed to relate rates to pore volume and accessible surface area. However, the complex shape of cellulases may create difficulty in penetrating such pores, and concerns have been raised about substrate changes during these measurements. Additionally, most measurement techniques measure gross surface area and may include non-specific adsorption, e.g., onto lignin.

Cellulases are often utilized as a mixture of enzymes having different activities, and the enzyme structures differ between microorganisms that express enzymes of a given family. While the mechanisms of hydrolysis and the relationship between the structure and function of various cellulases have been extensively studied, many details of enzymatic activity are still poorly understood. The enzymatic hydrolysis of cellulose substrates is strongly affected by end-product inhibition and enzyme features. Low specific cellulase activity on cellulose is an important factor that limits the effectiveness of hydrolysis. One way to circumvent this low specific activity is to recycle and reuse the enzyme. However, non-productive cellulase adsorption plays an important role in the development of ways to reuse enzymes and affects recycle efficiency.

Besides the complexity of the different types of cellulases, activity on the substrate is also complicated by substrate characteristics. Due to resistance from the complex structure and composition of natural cellulosic biomass, the lignocellulose substrate should be pretreated to make it as susceptible as possible to the action of the enzymes. Many pretreatment methods have been developed. For example, increased accessibility of lignocellulose substrate can be achieved by solubilizing hemicellulose in harsh acidic conditions.

Cellulase adsorption on lignocellulosic substrates containing high content of natural materials has not been extensively studied. Typically, lignocellulosic substrates contain a much higher content of lignin compared to "model" cellulose substrates. Lignin may inhibit enzymatic hydrolysis of lignocellulosic material. Cellulases are not only adsorbed to the cellulosic part of the substrate, but are also adsorbed to the lignin. Lignin not only shields the cellulose but also acts as a competitive adsorbent. However, lignin does not appear to restrict the extent of hydrolysis of the carbohydrate moiety if sufficient cellulase is present. Cellulolytic enzymes bind strongly to lignin. When adsorption profiles are compared, much more enzyme protein is associated with hydrolyzed residues of lignocellulosic materials than that of model cellulose. For example, β-glucosidase has a high affinity for various lignin fractions, while it does not bind to polysaccharides.

Generally, lignin may play an important role in enzymatic hydrolysis of lignocellulosic material (Sutcliffe & Saddler, Biotechnol. Bioeng. Symp. $8^{th}$, 17:749-62 (1986);). It has been shown that the enzymes are not only adsorbed to the cellulosic part of the substrate, but also bind strongly to lignin (Boussaid et al, *Optimization of hemicellulose sugar recovery from a steam-exploded softwood*, Proceedings of the Biomass Conference of the Americas, 3rd, Montreal, Aug. 24-29, 1997); Chemoglazov et. al., Enzyme Microb. Technol., 10:503-507 (1988); Deshpande, M. V. and K. -E. Eriksson, "*Reutilization of enzymes for saccharification of lignocellulosic materials,*" Enzyme and Microbiol. Technology, 6: 338-340, (1984); Sutcliffe & Saddler, Biotechnol. *Bioeng. Symp.* $8^{th}$, 17:749-62 (1986)). Specially, β-glucosidase appears to have a high affinity for various lignin fractions while it does not bind to polysaccharides (Sutcliffe & Saddler, Biotechnol. *Bioeng. Symp.* $8^{th}$, 17:749-62 (1986). The inactivation of cellulases by lignin has been reported (Avgerinos, G. C. and D. I. C. Wang, "*Selective solvent delignification for fermentation enhancement,*" Biotechnology and Bioengineering, 25(1): 67-83, (1983); Excoffier, G., B. Toussaint, et al. "*Saccharification of Steam-Exploded Poplar Wood.*" Biotechnology and Bioengineering, 38(11): 1308-1317, (1991); Sutcliffe & Saddler, Biotechnol. *Bioeng. Symp.* $8^{th}$, 17:749-62 (1986). It appears that different types of lignin and forms of lignin may have influenced adsorption of cellulase components (Chemoglazov et al., Enzyme Microb. Technol., 10:503-507 (1988); Sutcliffe & Saddler, Biotechnol. *Bioeng Symp.* $8^{th}$, 17: 749-62 (1986). Previous work on the hydrolysis of cellulose has shown that hydrolysis of pretreated substrates is improved when proteins are present. For example, it is reported that lignin peroxidase blocks lignin binding in biomass to enhance ethanol yield from SSF (WO 94/29474). That BSA addition results in the same level of hydrolysis yield as increasing surfactant addition is also indicated by Eriksson (Eriksson, T., J. Borjesson, et al. "*Mechanism of surfactant effect in enzymatic hydrolysis of lignocellulose,*" Enzyme and Microbiol. Technology, 31(3): 353-364, (2002)). It is most likely that the lignin blocking effect of protein in lignocellulose hydrolysis is explained by the protein's ability to block the non-specific adsorption sites of the non-cellulose fraction of the substrate and enhance the amount of cellulase available to absorb on the cellulose fraction (Eriksson et al. 2002; Kawamoto, H., F. Nakatsubo, et al. "*Protein-adsorbing capacities of lignin samples,*" Mokuzai Gakkaishi, 38(1): 81-4, (1992); Zahedifar, M., F. B. Castro, et al. "*Effect of hydrolytic lignin on formation of protein-lignin complexes and protein degradation by rumen microbes.*" Animal Feed Science and Technology, 95(1-2): 83-92, (2002)). Of course, the mechanism of protein interaction with lignin to enhance enzymatic digestibility is an object of intense research and speculation.

Lignin plays an important role in enzymatic hydrolysis of lignocellulosic material, as reported in Sutcliffe & Saddler, Biotechnol. *Bioeng. Symp.* $8^{th}$, 17:749-62 (1986). Comparative adsorption profiles demonstrated that much more enzyme was retained with hydrolyzed residues, compared to that of model pure cellulose, as reported in Abdel & Saddler, Int. Conf. Biotechnol. Pulp Pap. Ind., $7^{th}$, C239-C242 (1998). In a study by Chemoglazov et. al., Enzyme Microb. Technol., 10:503-507 (1988), endoglucanases that adsorbed on lignin lost activity. The inactivating effect of lignin was observed also with steam-exploded substrate, but not if the latter was acid-treated, nor with the lignocarbohydrate complex. Sutcliffe et al., Biotechnol. Bioeng. *Symp.*, 17: 749-762 (1986), report that adsorption of cellulases on different lignin preparations from steam-treated hardwood is influenced by the nature of the lignin and β-glucosidase was most affected by lignin. Thus, different types of lignin and forms of lignin may influence cellulase adsorption. Also, the form of the lignin, which contains distinct lignin and lignocarbohydrate complexes, seems to influence cellulases differently. It is generally agreed that the form and positioning of most lignin changes after steam-explosion, such that the lignin separates from cellulose to form agglomerates.

Several proposals have been made for solving the problem of ineffective and/or inefficient enzyme degradation of high lignin containing biomass materials. One of these is a pretreatment step that degrades or removes at least a portion of the hemicellulose and/or lignin from the biomass. For example, a combination of heat and acid pre-treatment of the lignocellulosic mass for a period of time has been used to hydrolyze hemicellulose. However, this process provides for only very limited removal of lignin, as reported in Grohmann et. al . . . Biotechnol. Bioeng. Symp. 17, Symp. Biotechnol. Fuels Chem., $8^{th}$, 135-151 (1986) and Torget et al., Applied Biochemistry and Biotechnology, 34-35:115-123 (1992).

Lignin removal from cellulosic fibers has also been proposed though using a caustic alkali, such as in Kraft pulping and paper making. However, this process does not produce simple sugars and does not separate the hemicellulose from the cellulose.

U.S. Pat. No. 4,668,340 issued to Sherman relates to biomass hydrolysis processing that produces almost exclusively hemicellulose sugars. Acid is introduced to the biomass, and is removed from each stage to be fed to the next in its sequence. The hydrolysis of cellulose is minimized in the process, and results in a cellulosic pulp containing over 90% of the feed α-cellulose.

U.S. Pat. No. 4,708,746 issued to Hinger relates to the specific hydrolysis of cellulose followed by treatment with high-pressure steam. However, the use of high steam alone does not provide for the complete hydrolysis of the cellulose substrate.

U.S. Pat. No. 5,125,977 issued to Grohmann et al., and U.S. Pat. No. 5,424,417 issued to Torget et al., relate to the prehydrolysis of a lignocellulosic biomass to solubilize the hemicellulosic sugars with concomitant release of some soluble lignin. Prehydrolysis renders the remaining cellulose more readily digestible with enzymes or other chemical means. U.S. Pat. No. 5,424,417 describes a process wherein lignocellulose is subjected to a prehydrolysis step by passing an acidic or alkaline solution through solid or lignocellulosic particles, with the continuous removal of soluble reaction products. The technique permits a less severe combination of pH, temperature, and time than conventional prehydrolysis. Extraction of hemicellulose and lignin occurs simultaneously in the same reactor and under the same conditions.

U.S. Pat. No. 6,022,419 issued to Torget et al. relates to a process in which a lignocellulosic biomass is fractionated by using a dilute acid, e.g., dilute sulfuric acid at 0.07 wt %, to convert cellulose into monomeric sugars in relatively high yields. However, cellulose hydrolysis using an acid catalyst is costly and requires special equipment. In addition, the desired sugars are labile in the harsh conditions, and significant amounts of unwanted and toxic by products typically form. If exposed too long, the glucose derived from the cellulose degrades into hydroxymethylfurfarol, which further degrades into unwanted degradation products including levulinic acid and formic acid. The acidic conditions similarly degrade xylose, which is formed from hemicellulose.

WO 94/29474 to Hinman relates to a process in which a treatment of lignocellulose minimizes binding of cellulase. A substrate is formed of cellulose, hemicellulose, and starch. A hydrolytic acid pretreatment agent is added to the substrate, as is a lignin peroxidase to block lignin binding sites in the biomass. Cellulase is added to the substrate using Simultaneous Saccharification and Fermentation (SSF) process conditions favorable for cell viability and conversion of ethanol.

Kadal et al., 53: 277-284 (1999), relates to the use of peroxide treatments to remove lignin under alkaline conditions during pulp bleaching. Under alkaline conditions, hydrogen peroxide reacts with both aliphatic and aromatic structures of lignin, leading to depolymerization and subsequent removal with water washing. Gould, Biotechnol. Bioeng., 26:46-52 (1984), reports the use of alkaline peroxide to remove lignin and improve enzymatic hydrolyzability of herbaceous residues. Ramos et al., Holzforschung 46:149-154 (1992), report the use of alkaline peroxide to steam explode hardwood. Yang et al., Biotechnology and Bioengineering 77(6): 678-684(2002), report the use of alkaline peroxide treatment to enhance the enzymatic digestibility of steam-exploded softwood substrates.

Generally, softwoods have been considered the worst-case scenarios as a feedstock for the bioconversion processes because their highly recalcitrant lignin reduces the efficiency of enzymatic hydrolysis. Schwald et al., Enzyme Systems for Lignocelluosic Degradation, Goughlan, M. P., Elsivier, N.Y., pp. 231-242 (1989), and Wu et al., Appl. Biochem. Biotechnol., 77-79, 47-54 (1998), report that a compromise in the pre-treatment conditions will likely be required, if softwood residues are to be considered as a potential feedstock for biomass processing, i.e., a medium severity process is needed between those optimized for high hemicellulose recovery and efficient cellulose hydrolysis.

According to the aforementioned pretreatment processes, cellulose substrates produced by pretreatment at medium severity (about log $R_0$=3.76) contain a high lignin content that limits cellulase accessibility to cellulose. The term "$R_0$" is used in the industry as an indicator of the relative severity of a treatment method for the processing of a biomass. Specifically, in the field of lignocellulosics and fractionation of wood components, "$R_0$" has been used to define a "severity parameter." This equation is described in Overend, R. P. & Chornet, E. (1987 Fractionation of lignocellulosics by steam-aqueous pretreatments. *Phil. Trans. R. Soc. Lond.,* 523-36.):

$$R_0 = t \cdot \exp[(T-100)/14.75] \quad (1)$$

where $R_0$ is the severity factor and is optimized at 3.8 for the prehydrolysis of hemicellulose, t is time of exposure in minutes, and T is temperature in degrees Centigrade.

SUMMARY

The present invention advances the art and overcomes the problems outlined above by providing an improved and more efficient method for enzymatically hydrolyzing high lignin-content biomass. For example, lignin blocking proteins may be used in a Simultaneous Saccharification and Fermentation (SSF) process to improve the yield of ethanol. These advantages are obtained without necessarily subjecting the biomass to harsh reaction conditions using a process that avoids significant production of toxic and unwanted degradation by-products. Additionally, a method of measuring cellulose surface area is disclosed, which may be utilized to develop an optimized pretreatment protocol.

In one embodiment, the method utilizes a protein and/or polypeptide that preferentially binds with lignin more readily than cellulose. A high lignin-content biomass is treated with the lignin blocking protein and/or polypeptide, for example by washing the biomass with a composition that comprises the lignin-blocking protein and/or polypeptide or by adding such materials to a saccharification broth. The lignin-blocking polypeptide and/or protein preferentially bind and thereby impede the lignin from further binding. Cellulose-hydrolyzing enzymes, such as cellobiohydrolase and β-glucosidase, may then hydrolyze cellulose more efficiently and rapidly. Without treatment of the lignin-containing biomass with a lignin-blocking polypeptide and/or protein, lignin in the biomass irreversibly binds a portion of the cellulose hydrolyzing enzymes, rendering them unable to hydrolyze cellulose. Protein and/or polypeptide treatment effectiveness is through lignin binding, thus reducing and/or eliminating non-productive adsorption of the cellulose hydrolyzing enzymes. The treatment of biomass with a lignin-blocking protein and/or polypeptide thus improves processing of relatively high lignin substrates by circumventing affinity of lignin for the enzymes. The polypeptide wash reduces enzyme use and/or improves performance because the enzymes do not become bound to the lignin, and remain available to hydrolyze the biomass.

In one aspect, the present method reduces enzyme loading in hydrolysis of high lignin content biomass. The amount of enzyme, such as cellulase, that is needed to provide hydrolysis is significantly reduced through treating the biomass with a lignin-blocking protein and/or polypeptide. These advantages reduce the overall costs of biomass conversion processes.

According to one embodiment, the method enhances the enzymatic digestibility of cellulose. This method includes the steps of treating a high lignin biomass with a lignin-blocking polypeptide and/or protein to provide a treated biomass having a blocked lignin component, and exposing the treated biomass to an effective amount of a hydrolyzing enzyme. By way of example, the hydrolyzing enzyme comprises β-glucosidase, cellobiohydrolase, endoglucanase, or a combination thereof.

In one embodiment, the method increases the yield of ethanol from a Simultaneous Saccharification and Fermentation (SSF) process about 5-25%. The lignin blocking polypeptide and/or protein may be added directly to the saccharification broth. The lignin blocking polypeptide and/or protein would preferably be added to the broth prior to the addition of the cellulose hydrolyzing enzyme and sugar-to-ethanol converting microorganism.

According to one embodiment, it is possible to accurately measure the cellulose surface area of a biomass feedstock. First, a lignin blocking polypeptide and/or protein is used to mask lignin sites that would otherwise adsorb cellulase. Second, cellulase is added and adsorbed with high specificity by the cellulose component of the biomass. A linear correlation between cellulose surface area and initial hydrolysis rate makes it possible to determine which pretreatment conditions lead to the greatest exposed cellulose surface area. Knowledge of the optimized pretreatment conditions may translate into cost savings for biomass processing plants.

Lignin-blocking polypeptides and/or proteins that are useful for these purposes include any polypeptide and/or protein, or lignin-blocking fragment thereof, having an affinity for lignin, and especially, for example, bovine serum albumin (BSA), soybean protein, amylase, chicken egg albumin, whey protein, and combinations thereof. Lignin-blocking polypeptides and/or proteins may be any polypeptide or protein that does not have appreciable binding affinity for cellulose, cellulase or other cellulose-hydrolyzing enzymes. By way of example, lignin-blocking polypeptides and/or proteins may have a molecular weight ranging from 2,000 Daltons to 300,000 Daltons. In some embodiments, the range may be that of a relatively high molecular weight, ranging from 55,000 Daltons to 80,000 Daltons, e.g., that of an albumin. However, lignin-blocking polypeptides and/or proteins having a lower molecular weight are also envisioned as useful in the practice of the present methods. These smaller lignin-blocking polypeptides, for example, may comprise a peptide fragment comprised of amino acids that is capable of effectively blocking or otherwise interfering with binding sites on the lignin. When fragmentary peptides are used, those having an amino terminal are preferred.

The lignin blockers, such as polypeptides, proteins, and fragments thereof, are not molecules that are otherwise intrinsically available to a lignin-containing biomass. The lignin blockers are usually provided in a relatively purified and isolated preparation of such materials, and in concentrations that are not present in nature. Thus, an incidental presence of protein and/or peptide, e.g., in a saccharification or fermentation media, would not provide the lignin-blocking action of the herein defined preparations. The lignin-blocking polypeptides, proteins and/or lignin-blocking fragments thereof are provided to the biomass as an externally supplied source of material not inherent to the native milieu of a biomass under ordinary processing circumstances, absent intervention by the hand of man.

The lignin-blocking polypeptides and proteins may be prepared in a composition with water, for example. The lignin-blocking polypeptide or protein that is used in the treating step may include a relatively low concentration of lignin-blocking polypeptide and/or protein, for example, 1% of the lignin-blocking polypeptide and/or protein by weight of the composition, or from 1% to 5% by weight of the composition.

The methodology employs compositions of a lignin-blocking polypeptide and/or protein, as well as compositions of a cellulose hydrolyzing enzyme, such as cellulase. As used here, a composition is defined as including a colloidal suspension, liquid phase of a mist, liquid/solid mist suspensions, vapor mixtures, and/or a solution, that includes the lignin-blocking protein and/or polypeptide or a lignin-blocking fragment thereof or a cellulose hydrolyzing enzyme.

Lignin is a phenolic polymer that can be derived by the dehydrogenative polymerization of coniferyl alcohol and/or sinapyl alcohol. Lignin has water-soluble and non-water soluble forms. Both water-insoluble and water-soluble lignins adsorb polypeptide and protein. Lignin presents non-specific adsorption sites for polypeptide and protein binding with, for example, lignin-treating polypeptides and proteins like bovine serum albumin and chicken egg albumin. Condensed lignin has the ability to adsorb polypeptide and protein from aqueous solutions. Dihydroxyphenyl groups and phenolic hydroxyl groups of the lignin molecule form binding sites that may be used to bind with and/or precipitate protein. Many different proteins can, therefore, be used to bind lignin and enhance enzyme access to cellulose in a biomass.

By way of example, a lignocellulosic biomass having high lignin content is defined as a biomass that comprises at least 5% by weight lignin, at least 10% by weight lignin, at least 20% by weight lignin, at least 40% by weight lignin, from 5% to 50% lignin, or from 10% to 50% by weight lignin.

In various embodiments, the lignocellulosic biomass comprises wood, agricultural and forestry residues, grasses such as switchgrass, ruminant digestion products, municipal wastes (paper mill effluent, newspaper, cardboard, etc.), or combinations thereof. For example, the lignocellulosic material may comprise birch, Douglas fir, corn stover, straw, or a combination thereof. These materials may be subjected to other preprocessing that decreases or increases their lignin content, for example, effluent from a paper mill. Thus, the method is applicable to environmental remediation processes, as well as the production of ethanol from biofuel.

It is envisioned that first treating a biomass with a lignin-blocking polypeptide and/or protein, or lignin-blocking fragment thereof, and then adding the cellulose hydrolyzing enzyme provides the highest efficiency in cellulose conversion. The lignin-blocking polypeptide and/or protein treatment of a biomass may also occur simultaneously with the addition of a cellulose-hydrolyzing enzyme to the biomass. However, a lesser advantage in conversion efficiency may be observed.

Treating a biomass with a lignin-blocking polypeptide and/or protein, e.g., by washing with a protein solution, may be followed by adding cellulase, or an enzyme of similar cellulose hydrolyzing activity. This treating step produces a hydrolysis yield from the cellulose that may be measured as percentage improvement in cellulase conversion efficiency. By way of example, a 20% improvement in percentage conversion of the total cellulose to carbohydrate may be obtained in comparison to the hydrolysis yield from cellulose of a biomass that is not treated with a lignin-blocking polypeptide and/or protein. As used herein, the term "a lignin-blocking polypeptide and/or protein" means any protein capable of providing a comparative improvement in cellulase conversion efficiency by binding with lignin to increase the availability of hydrolyzing enzyme. Saccharification of high lignin content substrates often benefits by at least a 5% improvement in conversion efficiency.

Still other embodiments pertain to improved processes for producing an organic compound from a high lignin-containing lignocellulosic biomass. The washing or lignin-blocking polypeptide and/or protein treating step may be preceded, for example, by a hydrolyzing step of contacting the lignocellulosic biomass with acid and steam to provide a treated solid biomass with a greater lignin component. The hydrolyzed biomass is then washed and treated with a lignin-blocking polypeptide and/or protein. This lignin-blocking treatment is followed by adding an effective amount of a hydrolyzing enzyme under conditions that are suitable for hydrolysis of the cellulose to produce carbohydrate at an efficiently high rate. The effective amount of hydrolyzing enzyme for a lignin-blocking polypeptide and/or protein-treated biomass, for example, is at least 25% less than the effective amount of hydrolyzing enzyme required for a similar conversion yield from a lignocellulosic biomass that is not treated with lignin-blocking polypeptide and/or protein.

Process steps in addition to the hydrolyzing step or steps may include extracting the carbohydrate, fermenting the carbohydrate in the presence of a sugar-to-ethanol converting microorganism for a period of time and under suitable conditions in a reaction mixture for producing ethanol and extracting the ethanol from the reaction mixture. Extraction may occur, for example, by ultrafiltration and/or fractional distillation. Cellulase-performance measured as a minimum cellulase concentration required to achieve a time-to-target cellulose conversion is improved from 5% to 75%, or from 20% to 75%, measured as a percentage difference compared to other processes that do not provide for a lignin-blocking protein and/or polypeptide treatment of the biomass.

Additional embodiments of the method comprise mixing particulate biomass having a high lignin content with a sufficient amount of an aqueous acid to produce a wet meal of lignocellulosic biomass, heating the biomass to remove hemicellulose, cooling and washing the solid, introducing a sufficient amount of a lignin-blocking polypeptide and/or protein to the residual solids to produce a treated biomass with a blocked lignin component, and adding an effective amount of a hydrolyzing enzyme to the treated biomass to provide carbohydrate.

Substrates pretreated under highly severe conditions are more accessible to cellulase enzyme, but have lower recovery of the hemicellulose-derived sugars. By contrast, pretreatment under less severe conditions generally liberates hemicellulose-derived sugars, but generates a solid residue that is not readily amenable to the hydrolysis of cellulose.

This effect in lignocellulose hydrolysis is explained by the protein's ability to block the non-specific adsorption sites of the non-cellulose fraction of the substrate and enhance the amount of cellulase available to absorb on the cellulose fraction. Lignin affinity for cellulase may be blocked by protein in the following three ways:

(1) close physical association with lignin;
(2) hydrophobic group adsorption to lignin; and
(3) precipitation involving dihydroxyphenyl groups and phenolic hydroxyl groups of lignin.

As to the latter mechanism, lignin is a complex phenolic polymer that may result from the dehydrogenative polymerization of coniferyl alcohol and/or sinapyl alcohol. Both water-insoluble and water-soluble lignin adsorb protein. The adsorption capacities vary depending on the different pretreatment methods and feedstocks. Furthermore, results show that added protein at low concentrations does not affect the rate of hydrolysis, which suggests that protein has no effect on the catalytic mechanism of the cellulolytic enzymes. Therefore, it is likely that protein blocks the non-specific adsorption sites on lignin to prevent unproductive binding of cellulases on lignin. The resulting improvement in hydrolysis may occur by introducing negative charges onto the lignin surface due to adsorption of protein. In turn, the negative charges prevent binding of negatively charged hydrolyzing enzymes. Without being bound by theory, it is believed that nonspecific binding of protein to lignin decreases unproductive binding of cellulases to lignin surfaces. Use of protein treatment in a process for lignocellulose conversion advantageously facilitates a lowering of the cellulase loading level to achieve the same target conversion percentage. For example, in the studies reported below, it was possible to lower the enzyme loading by 50% to achieve the same level of hydrolytic cellulose conversion with addition of protein at 2 g/L to pretreated lignocellulose substrates.

DETAILED DESCRIPTION

There will now be shown and described a method for increasing process efficiency in making useful products out of high lignin content lignocellulosic biomass. Efficiency is improved by treating the biomass with a lignin-binding protein and/or polypeptide. In some embodiments, this is accomplished with a protein wash of the biomass. Protein binding to lignin renders the lignin less available to bind cellulase or other cellulose-hydrolyzing enzymes. Thus, more cellulase is available to hydrolyze cellulose in a protein-treated biomass, and less cellulase is ultimately needed to provide a higher yield of component sugars from the biomass. The process is thus much more efficient than those in the prior art. In addition, initial hydrolysis rates are shown to correlate directly with cellulose surface area, so that the bioconversion pretreatment conditions (e.g., time, temperature, reagents) may be optimized by the instrumentalities disclosed herein.

The following discussion provides specific instances of this process demonstrating the instrumentalities according to the various embodiments by way of example, and not by limitation.

Figure 1:
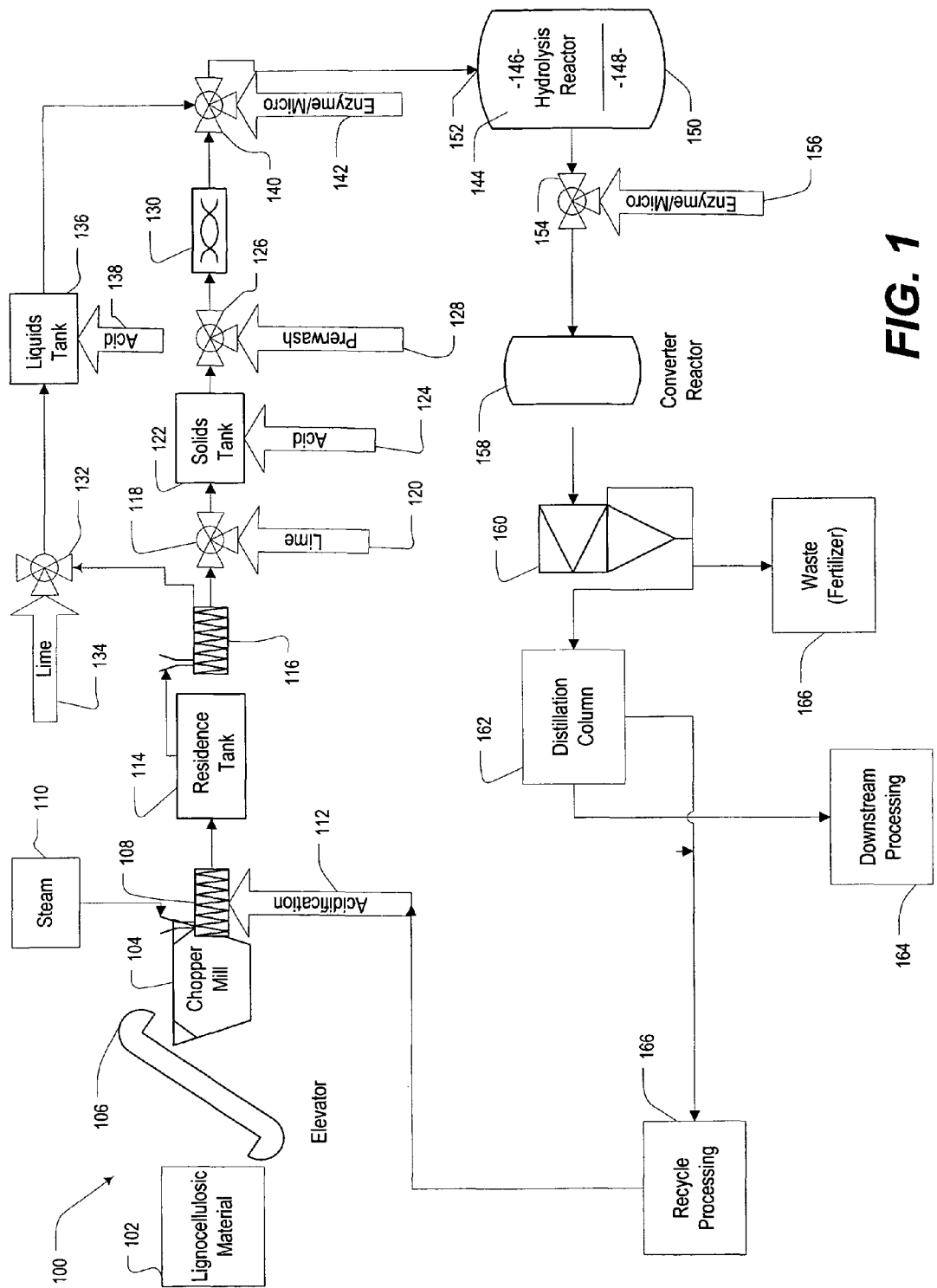
FIG. 1 is a schematic diagram showing process equipment that may be used according to one embodiment that uses BSA protein washing for lignocellulose conversion.

FIG. 1 shows one embodiment of a reactor system 100 that may be used for biomass conversion. A lignocellulosic material 102 is conveyed to chopper mill 104 by the action of transfer device 106, such as an elevator or slurry pipeline. The chopper mill 104 chops and/or grinds material of the lignocellulosic biomass pile 102, as needed, to a predetermined size that is suitable for downstream processing. It will be appreciated that the lignocellulosic material may be any feedstock that contains lignin and cellulose, particularly a high lignin content cellulose material. Accordingly, the reactor system 100 may be incorporated to accept any such feedstock, for example, to process wood, corn stover, straw, sawdust, bark, leaves, agricultural and forestry residues, grasses, ruminant digestion products, municipal wastes, paper mill effluent, newspapers, cardboard, or combinations thereof. Any agricultural, industrial, or municipal process that uses or discharges such wastes may be modified to incorporate reactor system 100.

A screw conveyer 108 transfers the chopped lignocellulosic material from chopper mill 104. Steam 110 may be added to screw conveyer 108, which may be configured to produce a steam explosion in the lignocellulosic material 102, for example, by processing the lignocellulosic material at high pressure sufficient to prevent boiling and temperature of 120° C. to 240° C. for a time ranging from one minute to sixty minutes or more. The screw extruder 108 optionally slurries the chopped lignocellulosic material with an acidification solution 112 that contains, for example, from 1% to 5% by weight of sulfuric acid mixed to homogeneity in water, e.g., to produce a pH of 1.2 to 1.4. The discharge from screw extruder 108 is flashed into residence tank 114, which is maintained at a temperature below 100° C. to cool the material and stop further reaction.

Residence tank 114 discharges into a screw conveyor 116, which at a first three way mixing station 118 mixes the slurry with a lime solution 120, e.g., one with sufficient lime to impart a predetermined pH of 10 to 11. The slurry is discharged into a solids holding tank 122 where it resides for an appropriate time permitting the lime to remove deleterious byproducts of acid hydrolysis. Additional acid 124, such as sulfuric acid, may be added into the solids holding tank 122 to adjust pH into a range from 5 to 7. The solids holding tank 122 discharges into a second three way mixing station 126 for further mixing with a prewash solution 128 that contains a lignin-blocking protein and/or polypeptide, e.g., one imparting a 1% to 5% lignin blocking protein and/or polypeptide content by weight of the slurry. Further mixing occurs through turbulator 130, which discharges into a third three way mixing station 140. Alternatively, the turbulator 130 may be a flow-through reactor in which solids are retained for an interval of time with recycle of the protein prewash solution 128, a fluidized bed reactor with recycle of the protein prewash solution 128, or a stir-tank.

In turn, the third three way mixing station 140 introduces an enzymatic solution 142 that contains a prehydrolyzing enzyme, for example, cellulase or a mixture of cellulase and other enzymes including glucosidase. Alternatively, the enzymatic solution 142 contains an inoculum and growth medium including a microorganism capable of saccharifying the slurry for hydrolysis of cellulose by the in vivo production of such enzymes. The slurry travels to a heated hydrolysis reactor vessel 144, which may be one of a series of such reactor vessels, for an appropriate residence time permitting hydrolysis of the slurry. For example, this residence time may be from one to seven days. A series (not shown) of hydrolysis reactor vessels 144 may permit continuous batch processing. The hydrolysis reactor 144 may, for example, be a flow-through reactor in which solids 148 are retained for an interval of time with recycle of fluids, a fluidized bed reactor with fluid recycle, or a stir-tank.

Slurry discharge from the hydrolysis reactor 144 may be subjected to additional mixing at a fourth mixing station 154, which adds a second stream 156, such as an aqueous stream with additional enzymes or a microorganism-containing stream useful for conversion processes, i.e., the conversion of sugars into alcohols. The second stream 156 reacts in a converter reactor 158, for example, to convert sugars into alcohol or other organic compounds. Discharge from converter reactor 158 may be submitted to a vortex separator 160, which discharges solids to waste disposal where the solids may, for example, be used as a boiler fuel. Liquids from vortex separator are submitted to distillation column 162, which concentrates useful products, e.g., ethanol, for further downstream processing 164, such as a molecular filter to remove water. Remaining liquids and/or solids from the distillation column 162 are submitted to recycle processing 166, for example, to filter fine particulates and add acid for use of such liquids as the acidification solution 112.

It will be appreciated that the equipment shown generally in FIG. 1 may be used or adapted to implement a variety of known processes. The prior processes do not include use of a wash (prewash) composition, such as a lignin-blocking polypeptide and/or protein prewash solution 128, and may be adapted for such use according to the instrumentalities described herein. The aforementioned use of the washing composition, prewash solution 128, results in significant cost reductions in the overall process of producing sugars or fermented organic compounds from high lignin content lignocellulose by reducing enzyme use.

Generally, any high lignin cellulose saccharification process may be improved by using a polypeptide to block non-specific hydrophobic adsorption sites of materials on a cellulosic substrate to enhance availability of hydrolyzing enzymes for saccharification of cellulose. The process may for example, entail making pulp, making paper, treating effluent from a pulp manufacturing process, treating effluent from a process of making paper, a bioconversion process, a biopolymer process, a protein-binding analytic assay, an enzymatic analytic assay, a waste treatment process, and combinations thereof.

By way of example, use of a continuous stirred tank enzymatic hydrolysis reactor, or a series of such reactors, has been shown to produce substantially equivalent saccharification results to the use of a batch reactor that is essentially a residence tank; however, these equivalent results are achieved using lower concentrations of hydrolyzing enzyme. Up to three times less enzyme is required using the continuous stirred tank enzymatic hydrolysis reactor. This advantage is amplified in a system that uses a series of continuous stirred tank enzymatic hydrolysis reactors, for example, where the process design is such that a first reactor may saccharify up to 75% of the available cellulose and is followed by one or more downstream reactors to complete the conversion process. These instrumentalities accelerate the overall conversion process and result in a greater conversion efficiency. The downstream reactors may be other stirred reactors, batch reactors or plug flow reactors (not shown in FIG. 1). At these dilute enzyme concentrations, use of lignin blocking protein is particularly useful because dilute enzymes would, otherwise, preferentially bind to lignin and become unavailable.

As used herein, a biomass of lignocellulose having a "high-lignin content" is defined as a biomass having at least about 10% by weight lignin per weight of cellulose. By way of example, such a biomass is characteristic of ground hardwood. The modification of known processes to include use of prewash solution 128 substantially improves cellulose conversion efficiency in processing high lignin content cellulose.

Among the processes for producing ethanol from lignocellulosic substrates (e.g., trees, grasses, and solid wastes) are those known as the Direct Microbial Conversion (DMC) or consolidated bioprocessing (CBP) process and the Simultaneous Saccharification and Fermentation (SSF) process. These processes can use a variety of microorganisms to convert organic material to ethanol. In the DMC/CBP method, a single microbial system both produces cellulase enzyme and produces ethanol as a fermentation product. The SSF method utilizes two biological elements, one that is based on cellulase enzyme and the other, which ferments sugar to ethanol.

As an alternative to adding cellulase in enzymatic solution 142, cellulase may be produced using a biomass fermentation process, for example, in a DMC process as described in Brooks et al., Proc. Annu. Fuels Biomass Symp., $2^{nd}$ (1978), or an SSF process as described in Ghose et al., Biotechnol. Bioeng., 26 (4): 377-381(1984). These processes may be used, as modified by the use of protein treatment, such as with a washing or prewashing step with a composition comprising a lignin blocking polypeptide and/or protein, according to the principles described herein. One example of an organism that is useful in converting organic matter to ethanol by way of the DMC process is *Clostridium thermocellum*. Other examples of suitable microorganisms that may be used with the DMC process option include *Fusarium oxysporum* and *C. cellulolyticum*. In addition, such organisms can be used in co-culture with *C. thermosaccharolyticum* or similar pentose-utilizing organisms such as *C. thermohydrosulfuricum* and *Thermoanaerobacter ethanoliticus*. An example of another microorganism that may be used in the practice of the claimed method according to the SSF process is *Sacchararomyces cerevisiae* (which produces ethanol).

A variety of suitable growth media for microbial digestion processes are well known in the art. Generally, a suitable growth medium is able to provide the chemical components necessary to maintain metabolic activity and to allow cell growth. One effective growth medium contains the following components per liter of water:

TABLE 2

| protein treated wood * | 5.0 g. |
|---|---|
| $NaH_2PO_4$ | 0.3 g. |
| $K_2SO$ | 0.7 g. |
| $NH_2SO_4$ | 1.3 g. |
| Yeast extract | 2.0 g. |
| Morpholinopropanesulfonic acid (MOPS) | 2.0 g. |
| Cysteine Hydrochloride | 0.4 g. |
| $MgCl_26H_2O$ | 0.2 g. |
| $CaCl_26H_2O$ | 0.1 g. |
| $FeSO_4$ | 0.1 g. |

*Prepared in a plugflow reactor at 220° C., 9 seconds residence time with 1% $H_2SO_4$ The medium noted above is set forth by way of example. Other suitable growth media may be used as well, including industrial media based on corn steep liquor.

According to other embodiments, a biomass that has been treated for enzymatic hydrolysis is further processed to produce an organic molecule, for example, in the converter reactor 158. As shown in FIG. 1, pH is altered by the lime solution 120, which may also occur downstream of positions shown in FIG. 1. Any of the known cellulases or cellulase complexes may be used in the enzymatic solutions 142 or 156. For example, cellulase digestion may be performed for one to three days at a temperature that is optimal for the cellulase employed. The sugar-containing solution is then separated from the residues, for example, by filtration, sedimentation, or centrifugation. The sugar solution may be recovered as sugars or it may be fermented to produce a desired organic chemical.

According to various embodiments and instrumentalities, the lignocellulosic material 102 may be woody biomass, herbaceous biomass (e.g., forage grass), and waste material (e.g., municipal solid waste). The size range of the lignocellulosic raw material varies widely and depends upon the type of material used as well as the requirements and needs of a given process. The size of the lignocellulosic raw material particles discharging from chopper mill 104 prior to downstream processing ranges from less than a millimeter in diameter to several inches in diameter. Particle size of the lignocellulosic raw material after processing through screw extruder 116 is in the range of one to four millimeters. A preferred lignocellulosic raw material is a woody biomass material comprised of particulate hardwoods. Exemplary hardwoods include poplar, oak, maple, and birch.

As used herein a "significantly reduced amount" of cellulase or other cellulose-hydrolyzing enzyme is an amount of enzyme that is less than that required to hydrolyze a high-lignin biomass that has not been treated with a lignin-blocking polypeptide and/or protein. More specifically, the "significantly reduced amount" of hydrolyzing enzyme constitutes the difference between the amount of cellulase needed to hydrolyze at least 50% of the cellulose in a high-lignin cellulosic biomass that has been treated with a lignin-blocking protein and/or polypeptide and the amount of cellulase or other cellulose-hydrolyzing enzyme needed to elicit the same amount of cellulose hydrolysis of a high-lignin cellulosic biomass that is not treated with a lignin-blocking protein and/or polypeptide. In particular embodiments, a "significantly reduced amount" of cellulose hydrolyzing enzyme is about 20% to about 50% less enzyme than is needed to hydrolyze cellulose in a lignocellulosic biomass not treated with a lignin-blocking protein and/or polypeptide. This improvement is made possible by use of the lignin blocking protein and/or polypeptide treatment composition, in this case a prewash solution, 128, shown in FIG. 1.

The lignocellulosic material is preferably ground before being submitted to downstream processing, e.g., as by use of chopper mill 104. If the nature of the lignocellulosic material is such that it will break down under the conditions of downstream processing, then grinding is not necessary. The particle size may not be critical but hydrolysis generally proceeds faster and perhaps to higher yields with a smaller particle size, so an economic optimization may be reached between the costs of grinding the lignocellulosic material and the cost advantages of higher throughput. Smaller particle sizes inherently provide more surface area for cellulase to attack and degrade cellulose.

Appropriate particle sizes vary with the feedstock and its inherent physical properties, as well as the flow conditions. In most processes, particle sizes appropriate for ground wood are in the range of about 0.1 mm to 30 mm preferably in the range of 0.5 mm to 4 mm. Other materials may be larger or smaller depending on the particular materials, particularly those having at least one thin dimension such as paper or straw. If one relies on the effects of gravity or floatation to cause movement of the solid lignocellulosic material with respect to the liquid, then particle size may need to be adjusted appropriately to permit solid/liquid movement during hydrolysis. Optimum sizes depend on the particular lignocellulosic material used and the reactor size and construction and are readily determinable by routine empirical studies for a reactor and reactor flow conditions.

The cellulosic materials may include hardwood, grasses, softwood, waste paper and pulp, municipal wastes, agricultural wastes such as straws, corn cobs, stover, biomass of all types, etc. and mixtures thereof. The choice of cellulosic material depends upon the availability and cost of the particular cellulosic material being processed. The advantages of the present lignin-blocking polypeptide and/or protein treatment methods are most evident in cellulosic biomass having a lignin content of at least 5%, 10% or more, e.g., 11%, 12%, 15%, 17%, 20%, 24%, 25%, 30%, 35%, 40%, 45%, 50%, 60%, 70%, or more. The lignin-blocking treatment methods may also be used to process both raw and partially processed cellulosic materials having lower lignin content, e.g., 7%, 6%, 5% or less.

In some embodiments, the reactor vessels 144 and 158 generally may have a solids content of about 5% to 50%, preferably 8% to 50%, when the solids are present with the liquid at the end of the hydrolysis. The higher solids content is generally more desirable but the concentration may be limited by reactor design and the need for fluid to heat the solids. At the beginning of the hydrolysis, the solids content may range from 0% to 100% by weight, as the reactor may initially contain only the lignocellulosic solids or the fluid.

In still other embodiments, enzymatic solution 142 including cellulase is added to a pH adjusted slurry. The cellulase digests cellulose to sugars according to manufacturer's instructions for the digestion of cellulose. Any of the known cellulases, cellulase complexes, or other cellulose hydrolyzing enzymes, may be used. The digestion occurs, for example, over one to seven days at a temperature optimal for the cellulase to produce a sugar-containing solution. The sugar containing solution is separated from the residues, for example, by filtration, sedimentation or centrifugation. The sugar-containing solution may be processed to recover sugar or further reacted or fermented to produce a desired organic chemical, such as an alcohol.

In fermentation processes, for example, the fermenting microorganism in second enzymatic solution 156 may be the same as was used in the enzymatic solution 142, but there may be a change in process conditions, such as a conversion from aerobic to anaerobic process conditions in the converter reactor 158. Cellulose digestion primarily produces glucose in the solids tank 122 and hydrolysis reactor 146. A much wider variety of microorganisms may be used to produce an even wider assortment of organic compounds in the converter reactor 158. The residue digest may be fermented in any manner known per se to utilize glucose. If so desired, the discharge from screw extruder 116 may be separated into liquid and solid components for separate process streams and recombined at a downstream position.

As an alternative to separate cellulase digestion and fermentation, both reactions may occur concomitantly in simultaneous saccharification and fermentation processes, for example, within the hydrolysis reactor 144. Any fermentation that is operable in conditions suitable for cellulase is acceptable. The conditions and concentrations in simultaneous saccharification and fermentation (pH, temperature, etc.) may be measured and adjusted to be optimized for either saccharification or fermentation or for overall optimization. The conditions may be changed as the process progresses.

The following description of the specific embodiments teaches by way of example, not by limitation. It will be appreciated that these examples are applicable to a variety of saccharification and fermentation processes. Therefore, such adaptations and modifications should and are intended to be comprehended within the meaning and range of equivalents of the disclosed embodiments. It is to be understood that the phraseology or terminology employed herein is for the purpose of description and not of limitations.

All references mentioned in this application are incorporated by reference to the same extent as though fully replicated herein. In the following examples, Laminex cellulase was purchased as Cytolase™ (a trademark of Genencor located in San Francisco, Calif.). The specific activity of the cellulase enzyme was approximately 28 international filter paper units (IFPU)/ml, as determined by National Renewable Energy Laboratory's Laboratory Analytical procedures LAP-006 (NREL, 2001). β-glucosidase was purchased as Novozyme 188 Sigma™ (a trademark of Novozyme located in Franklin, N.C.), and was used in the present preparations at a ratio of 1:1.75 (FBUase:CBUase). However, compositions of hydrolyzing enzyme that have a ratio of 1:1 to 1:10, or 1:1 to 1:2 are also contemplated. The remaining reagents specified by chemical name were purchased in research grade purity on commercial order from national laboratory supply houses. Cellulose powder (α-cellulose), used as a control substrate, was obtained from Sigma Chemical Co. of St. Louis, Mo.

The particular ratio of the enzymes can be adjusted on a case-by-case basis, for example, to optimize the amount of activity needed with a particular microorganism that is being used. In some cases, no β-glucosidase may be used because of the microorganism being used.

The yeast used in the simultaneous saccharification and fermentation (SSF) Examples were *Saccharomyces cerevisiae* $D_5A$ and *Brettanomyce custersii* (CBS 5512), as described in Spindler et al., Biotechnology Letters, 14: 403-407(1992) and U.S. Pat. No. 5,100,791, which is hereby incorporated by reference to the same extent as though fully disclosed herein. These references show ethanol production from polysaccharides in a single-step process in which an isolate of *Brettanomyces custersii* is used in combination with a carbohydrase to simultaneously saccharify and ferment the polysaccharide. This isolate of *B. custersii* can ferment cellobiose and glucose to ethanol. A medium containing 4% cellulose was inoculated with *B. custersii* CBS5512, and cellulase was added. After 5 days the medium contained 33 g ethanol per liter. Several other yeasts showed inferior rates and yields of ethanol.

The protein treatment composition may be prepared as a wash, such as a solution, prepared in distilled water. By way of example, one such wash solution was prepared by dissolving 10 gram (g.) of bovine serum albumin in one (1) liter (1000 mls) of distilled water. For example, where the biomass being washed has a weight of about 100 grams, the above protein washing composition would be prepared and the biomass would be washed with two liters of the described 1% BSA solution.

EXAMPLE 1

High Lignin-lignocellulosic Biomass Treatment With a Lignin-binding Protein

The present example demonstrates the utility of using a protein treatment, such as a protein/polypeptide washing step, to enhance the efficiency of cellulase activity in various high-lignin content lignocellulosic biomass sources. As compared to prior methods that attempt to degrade and remove the lignin content, the present method blocks the lignin by protein binding that prevents lignin from scavenging digestion enzymes. This example compares the protein prewashing methodology in the form of a wash pretreatment. Prior art techniques that include biomass processing with acid hydrolysis and/or steam explosion may be advantageously modified to include the protein prewash step as described below. Results show that similar efficiencies may be obtained by using substantially less cellulase enzyme when high lignin content biomass is prewashed with a protein solution that contains lignin-binding protein.

Biomass from two types of plants were examined: corn stover (CS) and Douglas fir. The CS samples differed in composition, as reported in Table 3. For each sample, chemical analysis was performed to determine beginning concentrations of cellulose, lignin and hemicellulose at the end of acid pretreatment, prior to protein washing, and prior to hydrolysis by cellulase. Cellulose content, lignin content, and hemicellulose content were determined by National Renewable Energy Laboratory's Laboratory Analytical Procedures LAP-002 & 003 (NREL, 2001).

In one instance of the results, pretreatment of CS (1) was with 1% $H_2SO_4$ (aq) at 140° C. for 40 minutes, or 0.1% $H_2SO_4$ at 160° C. for 80 minutes, as indicated in Table 3. The solid residue was washed with water (15 times by weight) to remove acidic groups before enzymatic hydrolysis. For sample CS (2), pretreatment was done by using a flowthrough reactor with water at 215° C. at a rate of 25 ml/min. Sample CS (2) was not acidified. Sample CS (3) was pretreated using a solution with 0.1% $H_2SO_4$ (aq) at 25 ml/min for 20 min. Sample CS (4) was pretreated under basic conditions simulating an AFEX process that entailed an ammonia loading range of 1 unit of ammonia for one unit of dry biomass, with system moisture content equal to 60% by weight. Temperature for this process was 90° C. and treatment lasted for 5 min.

The Douglas fir (*Pseudotsuga menziesii*) sapwood and heartwood were chipped and screened to a relatively homogeneous chip size of 4×4×1 cm. The chips were steam exploded in batches of 50 g dry weight using steam explosion conditions of 195° C., 4.5 min., and 4.5% (w/w) $SO_2$ as previously described in Boussaid et al. (*Optimization of hemicellulose sugar recovery from a steam-exploded softwood*, Proceedings of the Biomass Conference of the Americas, 3rd, Montreal, Aug. 24-29, 1997). These steam explosion conditions were chosen out of 13 experimental sets that included variations at five levels of temperature, $SO_2$ content and time. They provided the best recovery of overall sugars originating from hemicellulose and cellulose. The solid residue was washed with water (15 times by weight) to remove acidic groups before enzymatic hydrolysis.

Protein washing of selected samples occurred such that conversion efficiency in samples that were pre-washed with 1% bovine serum albumin could be compared to efficiency of samples that were not prewashed with bovine serum albumin.

Protein prewashing included washing each of the samples with 1% (w/w) protein solution by filtering the solution through a medium glass filter 3 times at room temperature. The solid residue was then further processed at 2% solid concentration (g dry weight/100 mL) in 50 mM acetate buffer, pH 4.8, containing 40 mg/mL tetracycline and 30 mg/mL cycloheximide. Flasks containing the buffered filtrates were pre-incubated at 45° C. on a rotary shaker at 150 rpm for 10 minutes. The enzymes were added to start the hydrolysis after acclimation. Aliquots of 0.5 mL were taken at different times (0, 0.2, 1, 4, 8, 12, 24, 48, 72 hour), immediately chilled on ice, and centrifuged at 5,000 rpm for 10 minutes. Total sugar analysis was performed on the resultant supernatants.

The enzyme preparations used for all hydrolysis studies were obtained from Genencor. Treatments were performed with a complete cellulase supplemented with β-glucosidase, (Novozyme™ 188) at a ratio of 1:1.75m (FPUase:CBUase). Enzymatic treatments were performed at different FPUase/g cellulose. Total FPU were calculated by adding the activities of both the Celluclast™ and Novozyme™ 188. The cellulase preparation possessed 28 filter paper units (FPU)/mL, whereas Novozyme™ 188 possessed 8 FPU/mL, and 480 β-glucosidase IU/mL, and was supplemented to avoid end-product inhibition due to cellobiose accumulation.

Total protein was measured using the Bio-Rad Protein Assay using BSA as standard, as per the manufacturers specified direction. The amount of unabsorbed protein in the supernatant was reported as a percentage of the amount of protein present in the substrate blank.

The sugar content of solids and acid insoluble lignin were determined using the Klason lignin procedure published by the National Renewal Energy Laboratory's Laboratory Analytical Procedures LAP—002 &003 (NREL, 2001). Approximately 300 mg of sample was ground to pass through a 40-mesh screen from the U.S. standard sieve series, available from Central Scientific of Ohio, weighed to the nearest 0.1 mg, and placed in 10 mL reaction tubes, which were then placed in a water bath, namely the Water bath Shaker 3540™ from Apogen Technology of Melrose Park, Ill. Three milliliters of 72% $H_2SO_4$ was added to the reaction tubes and the tubes were placed in a water bath at 30±1° C. for 1 h with frequent stirring. The tubes were emptied into 250 mL Erlenmeyer flasks containing 84 mL of deionized water, resulting in a 4% acid solution. These flasks were covered with aluminum foil and weighed before autoclaving at 120° C. for 1 hour. Following autoclaving, the weight loss was determined and readjusted by adding an appropriate amount of deionized water before vacuum filtering the mixture through a medium crucible. The solid residue was washed with 225 mL of hot water to remove any remaining acid. The crucible and total acid insoluble residue (not including ash) were baked in an oven at 105° C. for 12 hours. The weight of the remaining solids divided by the initial weight of the starting material gave the fraction of acid insoluble residue, which is typically designated as the Klason lignin content.

The sugar compositional analysis of all biomass solid and liquid samples was carried out by standard analytical procedures defined by National Renewal Energy Laboratory's Laboratory Procedures, LAP-001,002,003,005 & 012 (NREL, 2001). The filtrate from the acid insoluble residue test described above was loaded on a high performance liquid chromatography system, namely a Waters 2695™ from Waters of Milford, Mass., equipped with a pulsed refractive index detector (Waters 2410™ differential refractive) to obtain sugar compositions. Filtered liquid samples from hydrolysis were also run by this method. A mixed sugar solution of known composition of arabinose, galactose, glucose, mannose, and xylose was treated in parallel by exactly the same sequence as described in the acid insoluble residue procedure to estimate the sugar loss correction factor for acid hydrolysis and autoclaving. The filtrate samples were filtered through 0.2 μm NM filters obtained from Fisher of Pittsburgh, Pa., and a volume of 20 μL was charged to the sample vials that were then loaded into the high performance liquid chromatography system equipped with a pulsed refractive index detector to obtain sugar content. The column was equilibrated with de-ionized water at a flow rate of 0.6 mL/min. Aminex HPX-87P™ columns from Bio-Rad of Sunnyvale, Calif. were used for determination of sugar content.

Table 3 provides a comparison of various digestions that were performed on specified biomass materials. In some instances, the digestions were performed without a protein prewash.

TABLE 3

Increased Cellulase Efficiency Through Use of Protein Treatment with Bovine Serum Albumin (BSA)

| FEED | Pretreatment Condition | Protein Prewash | Beginning Cellulose (% dry weight) | Beginning Lignin (% dry weight) | Beginning Hemicellulose (% dry weight) | Cellulase Applied (FPU/g cellulose) | Percent Conversion of Total Cellulose |
|---|---|---|---|---|---|---|---|
| Corn Stover (1) | 1% $H_2SO_4$, 140° C. batch tube, 40 min | None | 56 | 28.2 | 11.2 | 15 | 82.3 |
| | | 1% Protein | | | | 15 | 91.7 |
| | | (BSA) | | | | 7.5 | 81.9 |
| Corn Stover (2) | Flow through reactor 215° C., flowrate of 25 ml/min, 20 min | None | 72.7 | 11.6 | 5.4 | 15 | 88.6 |
| | | 1% Protein | | | | 15 | 97.8 |
| | | (BSA) | | | | 10 | 90.4 |
| Corn Stover (3) | Flow through reactor 0.1% $H_2SO_4$ 190° C., flowrate of 25 ml/min, 20 min | None | 83.6 | 4.9 | 2.4 | 15 | 94.5 |
| | | 1% Protein | | | | 15 | 98.7 |
| | | (BSA) | | | | 10 | 95.7 |
| Corn Stover (4) | AFEX Ammonium loading range: 1:1 dry biomass moisture content 60%, Temperature range 90.5° C., 5 min. | None | 39.7 | 17.2 | 33.4 | 15 | 76.6 |
| | | 1% Protein | | | | 15 | 82.5 |
| | | (BSA) | | | | 10 | 74.3 |
| Douglas Fir (5) | Steam explosion (195° C., 4.5% $SO_2$. and 4.5 min | None | 56.3 | 46.1 | 8.2 | 20 | 54.2 |
| | | 1% Protein | | | | 20 | 73.5 |
| | | (BSA) | | | | 10 | 59.7 |

Legend. 1% Protein = 1% Protein washing substrates (BSA)

As indicated in Table 3, protein treatment provided enhanced enzyme efficiency for all substrates tested. Specifically, protein pretreatment followed by hydrolysis using a lower cellulase concentration (mg/ml) was able to achieve the same conversion efficiency as did a higher cellulase concentration in cases where there was no protein pretreatment. Relatively greater amounts of enzyme were saved with increasing amounts of lignin content of the substrate. The results from this study demonstrate that the protein treatment improved the level of cellulase enzyme hydrolysis of cellulose even in the most recalcitrant of lignocellulosic biomass materials. It is shown here that protein treatment saves 33-50% FPU activity or more to achieve roughly the same total conversion of cellulose, i.e., a total conversion of plus or minus about three percent of the total conversion without protein prewash. In the case of high lignin Douglas Fir, where the lignin content approached the weight of cellulose, a ten percent improvement in conversion efficiency was obtained using 50% less cellulase.

By way of example, sample CS (2) shows a percent conversion of 88.6% without protein prewash with use of 15 FPU/g, and a percent conversion of 90.4% with protein prewash using 10 FPU/g. The difference of 5 FPU/g or 33% less cellulase activity results in a slightly higher conversion efficiency of 90.4 (a 2% improvement with respect to 88.6%) due to the use of protein prewash. These results show using the protein prewash treatment may decrease cellulase consumption, for example, from 5% to 50%, or 20% to 30%, 20% to 40%, or even 50% or more to provide essentially the same yield measured as percentage conversion of cellulose to carbohydrate.

Table 3 also shows the same amount of cellulase activity providing percent conversion increases ranging from 4.4% in the case of CS (3) to 36% in the case of Douglas fir, which has a greater lignin content. By way of example, the Douglas fir sample was digested using 20 FPU/g cellulase with and without protein prewash. The protein prewash resulted in 73.5% percent conversion, as compared to 54.2% without the protein prewash to achieve a 36% improvement or percentage difference compared to the 54.2%.

EXAMPLE 2

Protein Treatment of High Lignin-containing Biomass

The present example demonstrates the utility of enhancing cellulose degradation and the efficiency of cellulase, or other cellulose-degrading enzymes, by inhibiting the binding capacity of lignin with protein/peptide having a non-specific lignin-binding affinity.

Two types of cellulose sources were studied. One type was α-cellulose—a purified cellulose without appreciable lignin content. The other biomass type examined was corn stover (CS). Seven samples were studied including α-cellulose without protein prewash, α-cellulose with protein prewash, CS with protein prewash, CS without protein prewash, and CS with protein washing during the course of the study period. The CS had a lignin content of approximately 10% to 17% by weight.

Conversion of cellulose samples including α-cellulose and CS were examined. Each sample was pre-treated with 0.1% $H_2SO_4$ at 180° C. for 40 min. Prewashed samples were prepared by washing the sample three times at room temperature with 1% (w/w) aqueous bovine serum albumin (BSA) protein solution. The solids remained on a medium glass filter at room temperature (the ratio of solid to protein solution was 1 g:20 mL, the range of protein-absorbing capacities of lignin were about 0.4 to 0.96 mg BSA/mg lignin). The solid residue was then further processed at a 2% solid concentration (g dry weight/100 mL) in 50 mM acetate buffer, pH 4.8, containing 40 mg/mL tetracycline and 30 mg/mL cycloheximide. Flasks containing the buffered filtrate were pre-incubated at 45° C. on the rotary shaker at 150 rpm for 10 min, and the enzymes were added to start the hydrolysis after acclimation. Aliquots of 0.5 mL were taken at different times (0, 0.2, 1, 4, 8, 12, 24, 48, 72 h), immediately chilled on ice and centrifuged at 5000 rpm for 10 min. Total sugar analyses were performed on the resultant supernatants. Identical procedures were performed during the analysis of all samples. Saccharification results were measured as a conversion of total cellulose.

The enzyme preparations used for all hydrolysis studies were obtained from Genencor. Treatments were performed with a complete cellulase supplemented with Novozyme™ 188 β-glucosidase, at a ratio of 1:1.75 (FPUase:CBUase). Enzymatic treatments were performed at 15 FPU/g cellulose. Total FPU were calculated by adding the activities of both the Celluclast™ and Novozyme™ 188. The cellulase preparation possessed 28 filter paper units (FPU)/mL, whereas Novozyme 188 possessed 8 FPU/mL, and 480 β-glucosidase IU/mL, and was supplemented to avoid end-product inhibition due to cellobiose accumulation.

Figure 2:
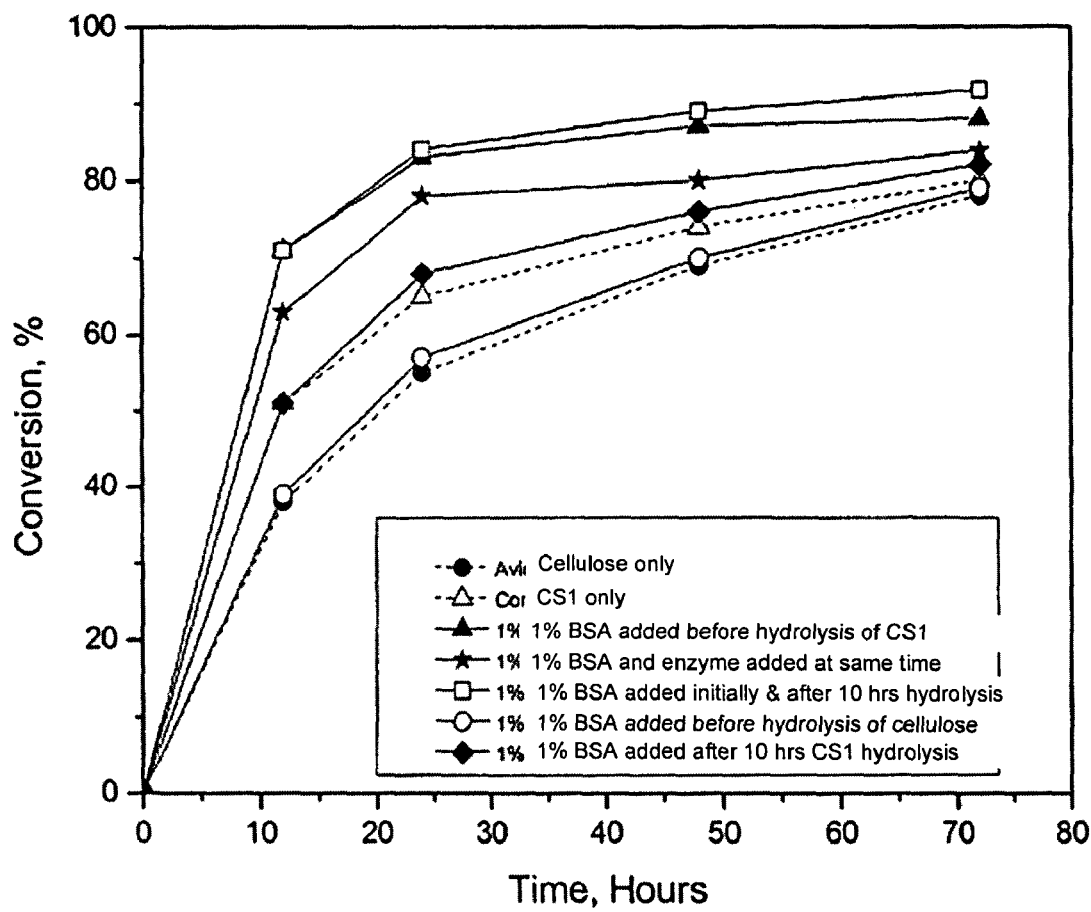
FIG. 2 shows solution concentration changes that result from hydrolysis of α-cellulose and corn stover (CS1), with and without protein (BSA) addition.

FIG. 2 shows the results. It will be appreciated that α-cellulose does not include an appreciable lignin component; however, the α-cellulose biomass sample showed a slight increase in conversion efficiency resulting from BSA washing. This increase is in the range of experimental deterministic uncertainty. As this difference is less than a 1% to 3% conversion efficiency over time, the BSA is deemed not to substantially interfere with cellulase-cellulose interaction. The CS1 samples, i.e., samples having a higher lignin content than does α-cellulose, show a conversion efficiency difference of about 15% after about 25 hours.

Treatment of pretreated corn stover with BSA prior to cellulase addition greatly enhanced the rate of hydrolysis, and the conversion of cellulose at 72 hours was improved to about 90% when treated with BSA versus only about 78% when the cellulase mixture was employed alone. When cellulase and BSA were added at the same time, the initial hydrolysis rate was significantly improved, and the final yield was about 5% higher than when cellulase was used alone. Adding BSA ten hours after cellulase addition had little effect on performance at the initial stages of hydrolysis but did improve the final yield by around 2%. FIG. 2 also shows that adding BSA to corn stover, which was treated with BSA before cellulase addition and then hydrolyzed for ten hours, enhanced the final yield by about 3% relative to a single washing with BSA. These results demonstrate that the greatest increases in coversion are obtained when the lignin-blocking protein and/or polypeptide is added to the substrate prior to addition of the cellulose hydrolyzing enzyme; however, increased conversion may be achieved when the lignin-blocking protein and the hydrolyzing enzyme are added simultaneously and/or when a lignin-blocking protein is added after the start of hydrolysis.

Lignin-blocking polypeptides and proteins that may be used as described herein have a preferred utility of enhancing efficiency of cellulose hydrolysis in biomass that contains at least about 5% lignin by weight. This principle is demonstrated in FIG. 2, where CS1 plus BSA achieved about a fifteen percent greater conversion efficiency than did CS1 without BSA.

More particularly, as an experimental control, the percent conversion (%) and the rate of conversion (time, hours) of the α-cellulose biomass with protein-treatment and without protein treatment was about the same. The sample including α-cellulose+BSA reached 38% conversion at 12 hours, and 53% at 25 hours. The sample including α-cellulose without BSA reached 37% conversion at 12 hours, and 52% at 25 hours. The corn stover including more than about 10 to 17% lignin, provides a much more significant difference in the percent conversion. A much greater amount of cellulose in biomass was converted in the lignin-blocking polypeptide and/or protein-treated, lignin-containing biomass compared to the biomass not treated with a lignin-blocking polypeptide and/or protein. Using the same amount of cellulase enzyme (20 FPU/g cellulose enzyme loading), an observable increase in cellulose conversion after about 12 hours was demonstrated. This increase in cellulose conversion continued over time. CS+BSA reached 70% conversion at 12 hours, and 81% at 25 hours. CS without BSA reached 50% conversion at 12 hours and 62% at 25 hours. Here, a difference in cellulose conversion of the protein-treated corn stover biomass of about 20% is demonstrated after 25 hours. This difference in the amount of cellulose conversion between the protein-treated and the non-protein treated biomass was maintained over the 70-hour period monitored.

EXAMPLE 3

Bioconversion of Steam-hydrolyzed Softwood With Protein Treatment

The present example further demonstrates the efficiency of bioconversion of a softwood lignocellulosic substrate that is pretreated with an acid catalyzed steam prehydrolysis step. The example provided here of a softwood lignocellulosic biomass was prepared from Douglas fir tree material.

A fir tree sample was prepared as described in Boussaid et al., *Optimization of hemicellulose sugar recovery from a steam-exploded softwood (Douglas fir). Making a Business from Biomass in Energy, Environment, Chemicals, Fibers and Materials*, Proceedings of the Biomass Conference of the Americas, 3rd, Montreal, Aug. 24-29, 1997. The biomass was then processed through a pre-hydrolysis treatment of steam explosion (195° C., 4.5% $SO_2$ for 4.5 minutes). The steam exploded, prehydrolyzed biomass was then treated with a 20 FPU/g cellulose loading. The percent conversion by enzymatic hydrolysis was 54.2% after 72 hours. In contrast, when the steam exploded steam hydrolyzed biomass was treated with a 1% bovine serum albumin preparation, and then treated with a much lower amount of cellulase, 10 FPU/g cellulose, a conversion of 59.7% was obtained (See Table 3). The results demonstrate a reduction of 50% enzyme loading producing slightly more conversion product from steam exploded biomass of Douglass fir.

EXAMPLE 4

Enzyme Utilization/Preservation as Assessed By Filter Paper Activity (FPU) With and Without Protein Treatment of Biomass The present example demonstrates that by pretreating a lignocellulosic biomass with lignin-blocking polypeptide and/or protein, the cellulase enzyme activity will be maintained in an active, unbound state. The relative activity of the enzyme (cellulase) is measured as filter paper activity (FPA %).

Figure 3:
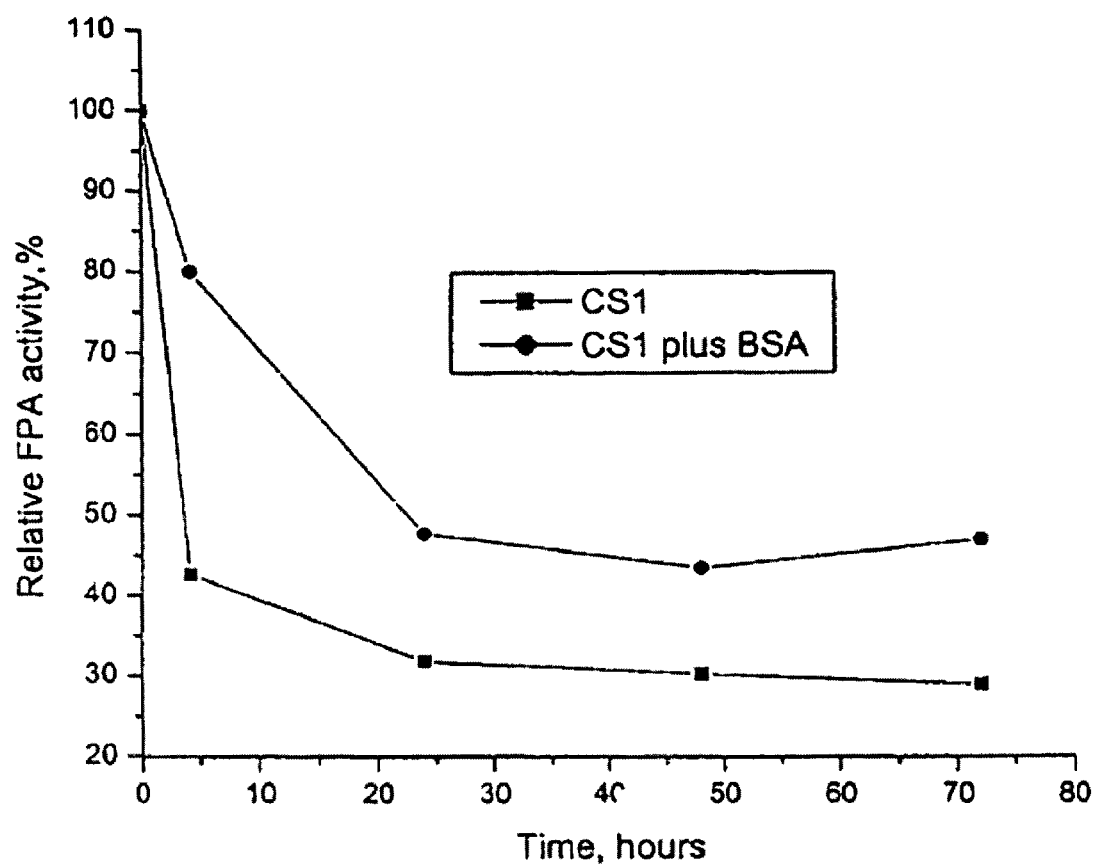
FIG. 3 shows filter paper activity (FPA) comprising changes during hydrolysis of corn stover with and without protein addition.

Corn stover (CS1), was prehydrolyzed with 0.76% $H_2SO_4$, at 160° C., for 10 minutes. Both the protein treated and the non-protein treated corn stover samples were examined starting with a 20 FPU/g cellulose enzyme loading. The amount of filter paper activity change was then monitored for both samples as a function of time. These results are shown as FIG. 3.

Relative FPA was preserved to a greater extent and for a longer period of time with biomass that had been treated with protein, compared to biomass that had not been treated with the protein. Relative FPA % of the CS1 sample fell from 100% to 42% after only about 4 hours, and then fell again to about 30% after 25 hours. In contrast, relative FPA % of the CS1 plus BSA fell only to about 80% after about 4 hours with the lignin-blocking protein treated biomass, and fell only to 50% relative FPA % after 25 hours (See FIG. 3).

These data demonstrate that protein treatment effectively binds lignin in the corn stover biomass, and thereby precludes the lignin from binding available cellulase. For this reason, cellulase FPU activity was preserved for a longer period of time. This factor presents substantial economic advantages in using lignin-blocking protein pretreatment of lignin-containing biomass in bioconversion to ethanol.

EXAMPLE 5

Protein in Solution and Bioconversion Efficiency in Lignin Versus Non-lignin Containing Biomass The present example is provided to demonstrate that a lignin-blocking polypeptide and/or protein, such as BSA, and the cellulase enzyme, are absorbed differently by a biomass that includes a lignin component, compared to a biomass that does not include a significant lignin component. This principle is demonstrated in the present example using α-cellulose, a biomass with little lignin, and CS, which does include at least 10% lignin.

Figure 4:
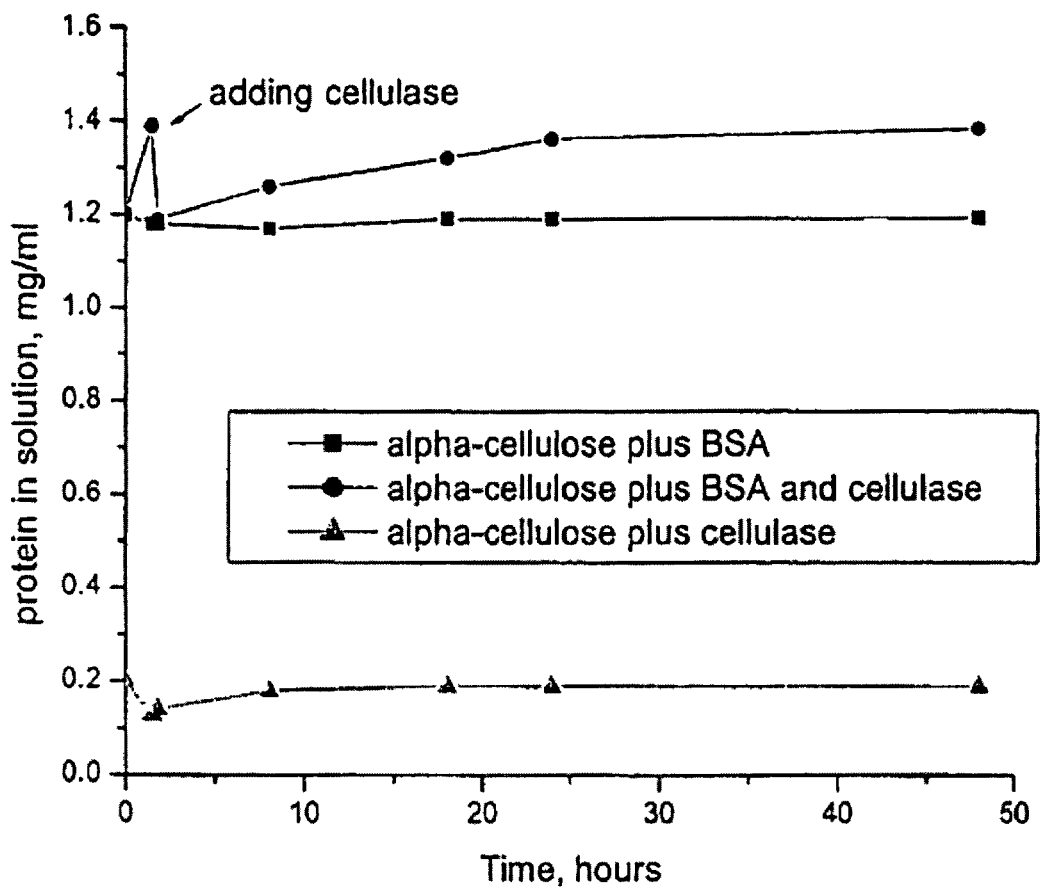
FIG. 4 shows total protein in supernatant during hydrolysis of α-cellulose with and without protein addition.

FIG. 4 demonstrates an analysis of total protein in solution over time during the hydrolysis of a biomass of α-cellulose. The FIG. 4 study was conducted using an initial cellulase enzyme loading of 20 FPU/g cellulose enzyme. FIG. 4 shows that in the absence of lignin in the biomass due to the use of α-cellulose, any protein that is added to the solution will not be adsorbed; it therefore remains a measurable component in the solution. At 0 hours, the α-cellulose plus BSA sample demonstrated a detectable amount of 1.2 mg/mL protein in solution, which increased to 1.4 mg/mL upon the addition of cellulase at 1.5 hours (FIG. 4). The amount of protein in solution then dropped to 1.2 mg/mL at about 1 hour. About the same amount of protein in solution value was obtained using α-cellulose treated with BSA to which no cellulase had been added. Over time, there was about a 0.1 to 0.15 mg/mL increase in the amount of measurable protein in solution in the α-cellulose sample to which both cellulase and a protein (BSA) treatment had been administered. No increase in the amount of measurable total protein in solution over time was demonstrated with the α-cellulose treated with BSA, but not cellulase.

FIG. 4 also shows that α-cellulose to which cellulase has been added results in a relatively static protein in solution detectable level over the entire time period examined. As shown, about 0.2 mg/mL total protein in solution was evidenced with this sample at 0 hours, and this amount was relatively the same at 50 hours (See FIG. 4).

Figure 5:
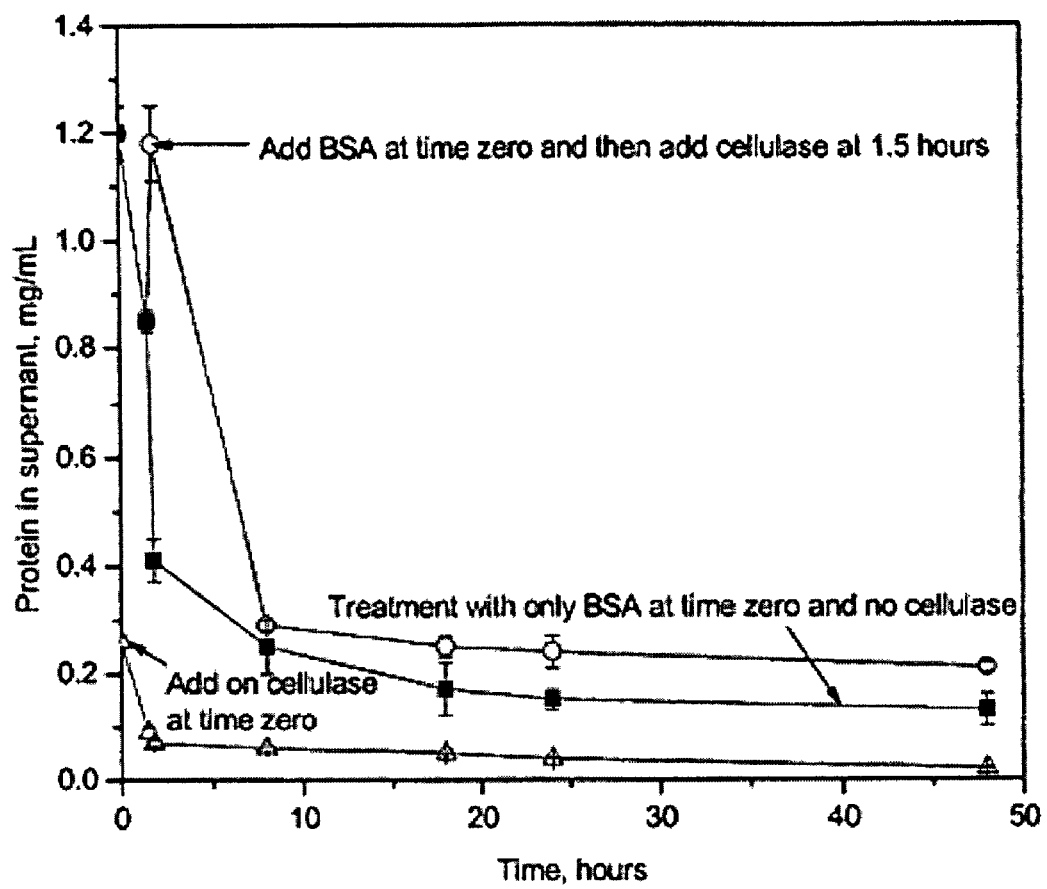
FIG. 5 shows protein in supernatant during hydrolysis of corn stover with and without protein addition.

FIG. 5 demonstrates the analysis of total protein in solution over time during hydrolysis of a biomass of corn stover (shown as CS1). The FIG. 5 study was conducted using an initial cellulase enzyme loading of 20 FPU/g cellulose. FIG. 5 demonstrates that in the presence of lignocellulosic biomass (CS), protein added in the form of the enzyme (cellulase) or protein wash (BSA), is adsorbed by the substrate so that it is undetectable in the solution. This reduction of total protein in solution is opined to reflect the adsorption of the BSA, the cellulase, or both, to the lignin component of the biomass. FIG. 5 demonstrates a significant reduction of protein (including cellulase and/or BSA) in solution using a biomass that includes a lignin component. A protein-treated (BSA) biomass of corn stover demonstrated an initial protein in solution measure of 1.2 mg/mL. This measure dropped initially to 0.9 mg/mL at about 1 hour, and then rose again to 1.2 mg/mL upon the addition of cellulase at about 3 hours. The protein in solution level fell dramatically at about 8 hours to about 0.2 mg/mL, and remained at this level over the entire period of the study, 50 hours.

Corn stover sample was also examined without having been treated with protein (BSA). Cellulase was added to this sample as well. The initial protein in solution value was much lower, at 0.2 mg/mL, at the 0 hour time point. This amount decreased to about 0.1 mg/mL after about an hour, and remained at this low level for the observed period of study, 50 hours.

For comparison, the addition of BSA, without subsequent addition of cellulase, showed a starting concentration of about 1.2 mg/mL that decreased steadily to about 0.1 mg/mL less than the sample containing both BSA and cellulase. The lower equilibrium level observed when BSA is used alone reflects the lack of a cellulase contribution (about 0.1 mg/mL), which would otherwise increase the level to that observed for the BSA and cellulase mixture.

Together, FIGS. 4 and 5 show that BSA protein has almost no effect on the rate of hydrolysis of α-cellulose. However, the rate of hydrolysis of CS1 was improved by the BSA prewash. These results suggest that protein has little effect on the catalytic mechanism of the cellulolytic enzymes, and confirm that the use of protein prewash improves cellulase availability to the substrate. Therefore, it is likely that protein-blocking of the non-specific adsorption sites on lignin is a key role of protein treatment in explaining the positive effect of protein on enzymatic hydrolysis of lignocellulose.

Overall, the biomass sample with lignin demonstrated much lower levels of protein in solution over the entire test period compared to biomass that did not contain a lignin component. Thus, proteins, in the form of BSA, cellulase, or both, are absorbed by the lignin component of the biomass, and therefore protein is not detectable in solution. The proteins are absorbed to the lignin component of the biomass. This conclusion is supported by the observation of detectable protein in solution when examining biomass that does not include a lignin component. The protein in solution was highest in the α-cellulose biomass that had been treated with the BSA protein and cellulase. The α-cellulose plus BSA treatment demonstrated a lower total protein in solution than the sample to which cellulase and BSA were added. The α-cellulose biomass to which only cellulase had been added demonstrated a consistently lower amount of detectable total protein, 0.2 mg/mL in solution over the entire test period. Here, the cellulase is acting to hydrolyze the available cellulose of the α-cellulose, unhindered by any lignin component.

EXAMPLE 6

Sequential Protein Addition and Treatment

To measure hydrolysis with just cellulase, 0.26 mg of cellulase was added per mL of a 2% suspension of Avicel or pretreated corn stover solids at time zero. The effect of bovine serum albumin (BSA) (Sigma, St. Louis, Mo.) addition was first determined by adding enough BSA to pretreated corn stover to make a 1% (w/w) solution 1.5 hours before and/or 10 hours after cellulase addition. Additionally, cellulase at a loading of 15 FPU/g cellulose was added at the same time as enough BSA to make a 1% solution to a 2% suspension of pretreated corn stover. Finally, 1.2 mg of BSA was added per mL of suspension at time zero followed by 0.26 mg of cellulase one and a half hours later. In this case, the mixture was quickly transferred to a medium crucible (Fisher Scientific Company, PA) before adding the enzymes to filter off the free liquid portion, and the solids were then washed three times with the supernatant.

The time course of enzymatic hydrolysis of cellulose in Avicel and pretreated corn stover were followed for a cellulase loading of 15 FPU/g cellulose with and without treatment of BSA. As shown in FIG. 5, treatment with BSA prior to cellulase addition had little effect on the conversion of Avicel throughout the reaction period. However, treatment of pretreated corn stover with BSA prior to cellulose addition greatly enhanced the rate of hydrolysis, and the conversion of cellulose at 72 hrs was improved to about 90% when treated with BSA versus only about 78% when the cellulase mixture was employed alone. Adding BSA after cellulase addition had little effect on performance at the initial stages of hydrolysis but did improve the final yield by a few percent. When cellulase and BSA were added at the same time, the initial hydrolysis rate was significantly improved, and the final yield was about 5% higher than for adding cellulase alone.

In addition, FIG. 5 shows that adding BSA to pretreated corn stover, which had been treated with BSA before adding cellulase and hydrolyzed for 10 hours, enhanced the final yield by about 3%. It also shows that the final yield still improved by around 2% even when BSA was added to pretreated corn stover after 10 hours of hydrolysis. Clearly, BSA addition was particularly effective when added before cellulase, consistent with it being irreversibly bound to lignin. Yet, adding BSA with cellulase still resulted in some gain in both rates and yields. Furthermore, adding BSA after hydrolysis began also enhanced rates whether pretreated corn stover was treated with BSA prior to hydrolysis or not. The latter result could be attributed to BSA attaching to lignin exposed during hydrolysis and reducing non productive cellulase adsorption later in the process. Alternatively or in addition to this, this observation could be due to BSA adsorbing on lignin following desorption of cellulase. In any event, these results support the idea that BSA attaches competitively to lignin in the presence of cellulase.

EXAMPLE 7

Bioconversion Process Control

The present example demonstrates a way to optimize economic efficiency in one bioconversion process.

A source of biomass feedstock is selected, usually based on cost and availability. Test batches of the feedstock are subjected to several different pretreatment protocols to expose cellulose, for example, AFEX, steam explosion or acid pre-hydrolysis. Each pretreatment method may be tested using various conditions, for example, by changing temperature, acid or other chemicals, concentration and time. Cellulase is added to the pretreated batches and the initial hydrolysis rate is measured to identify the pretreatment method that produces the highest initial hydrolysis rate. The rate may be measured by techniques known in the art, such as fluorescent spectroscopy.

Process controls may be established using empirical data to calculate hydrolysis rates and saccharification times involving any cellulosic substrate and hydrolyzing enzyme. This calculation may involve a surface area estimate or measurement. When surface area effects are accounted for, cellulase digestion of cellulose is frequently a reaction of first order kinetics. Different techniques for calculating cellulose surface area include, for example, a Bennet-Emmit-Teller technique that uses nitrogen on dry substrate to determine a gross surface area, not just the exposed surface area. Another technique is to use a Solute Exclusion Technique that makes pore geometry assumptions, ignores external surface area and uses a solute to measure gross surface area. A cellulase adsorption technique includes non-specific adsorption, such as lignin, and measures gross surface area as a function of quantifiable bound cellulase.

One way of calculating the maximum adsorption capacity for cellulase on cellulose is to use the Langmuir isotherm:

$$[E]_{ad} = \frac{[A]_{max} \cdot [S]_{total} \cdot [E]_{free}}{K_d + [E]_{free}}$$

where $[E]ad$ is the concentration of adsorbed protein (mg cellulase/mg cellulose); $[E]free$ is the concentration of unadsorbed cellulase (mg cellulase/ml); $[A]max$ is the maximal adsorbed cellulase (mg cellulase/mg cellulose); $[S]total$ is the total substrate concentration (mg/ml); Kd is the equilibrium constant (ml/mg cellulase).

When $[S]total >> [E]total$:

$$[E]_{ad} = \frac{[A]_{max} \cdot [S]_{total} \cdot [E]_{total}}{K_d + [A]_{max} \cdot [E]_{total}}$$

Figure 7:
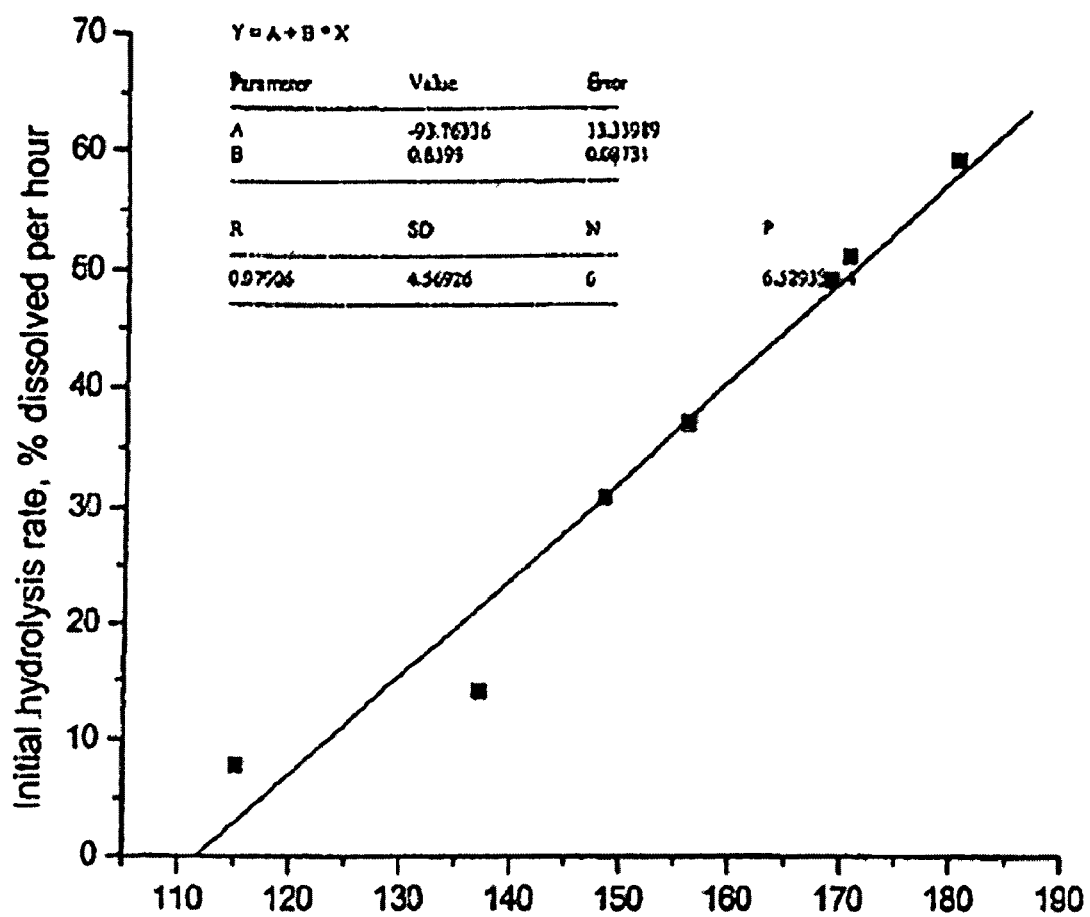
FIG. 7 shows the relationship between initial hydrolysis rate and maximum cellulase adsorption for pretreated corn stover, which had been subjected to a Bovine Serum Albumin prewashing.

One way of projecting hydrolytic activity, e.g., as a percentage of total cellulose dissolved over time, is to use one of the foregoing techniques to calculate directly or indirectly the surface area and use a mathematical model to map the surface area to hydrolysis rate. FIG. 7 shows one such model for a plurality of corn stover samples of different composition. A mathematical model exists as a linear correlation between cellulose surface area, which is measured as cellulase adsorption, and initial hydrolysis rate, such that the batch showing the highest initial hydrolysis rate is necessarily the sample with the most exposed cellulose surface area.

Figure 8:
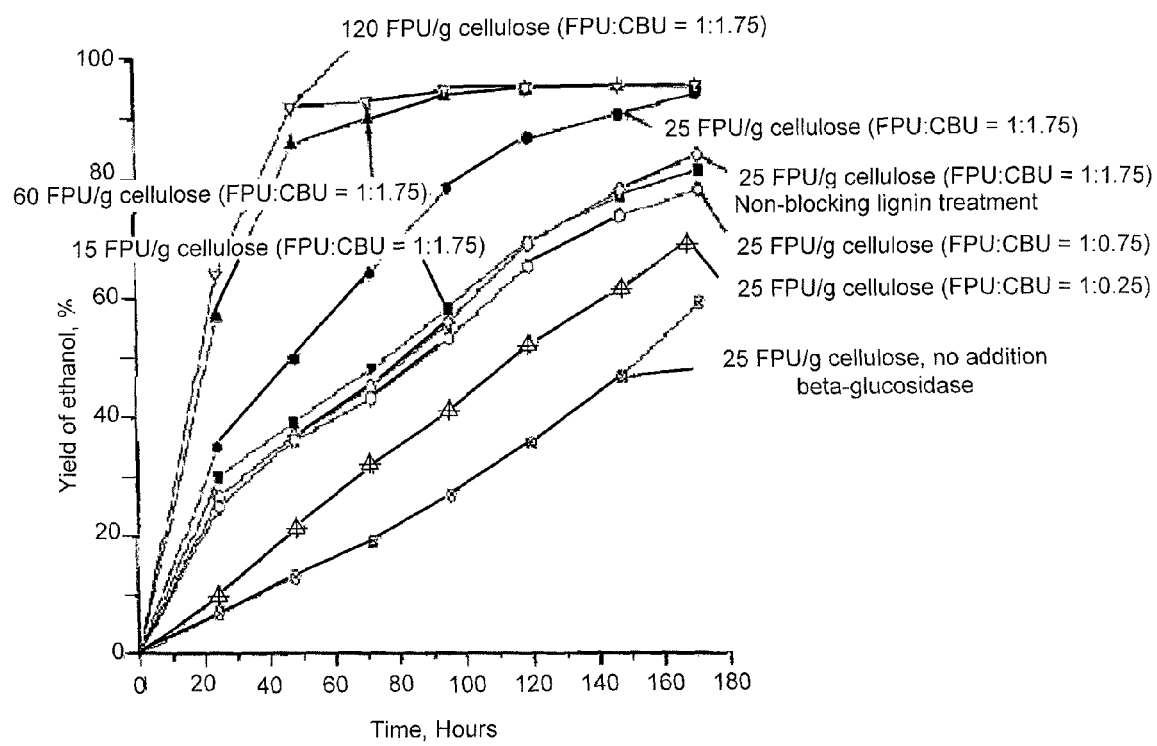
FIG. 8 shows the increased yield of ethanol when a lignin-blocking treatment is used in a SSF process.

The difference in relative hydrolysis rates may be further mapped to a cellulase composition that is particularly attuned to the type of biomass which is to be subjected to saccharification and characteristics of a plant or facility where the conversion takes place. FIG. 8 shows ethanol yield over time for corn stover that underwent hydrolysis under different FPU and CBU loadings. The corn stover was pretreated with 1% by weight sulfuric acid at 140° C. for 40 minutes. The loadings included different samples at 25 FPU/g cellulose with a ratio of FPU:CBU including 1:0, 1:0.25, 1:0.75, and 1:1.75. Additional loadings were studied at 15 FPU/g cellulose (FPU:CBU 1:1.75), 60 FPU/g cellulose (FPU:CBU 1:1.175 and 120 FPU/g cellulose (FPU:CBU 1:1.175). Unless otherwise indicated on FIG. 8, the samples were subjected to a 1% BSA prewash prior to saccharification.

FIG. 8 shows that a particular type of corn stover may receive, as substantial equivalents, hydrolyzing enzymes that contain either 15 FPU/g cellulose (FPU:CBU 1:1.175), 25 FPU/g cellulose (FPU:CBU 1:1.175) without protein prewash, or 25 FPU/g cellulose (FPU/CBU 1:0.025). The relative ratio of β-glucosidase activity in the cellulase mixture may affect ethanol yields and production rates significantly.

In a system that is populated with results for a variety of corn stover materials presented in the manner of FIG. 8, where each material is mapped to a hydrolysis rate, it is a simple matter to run a hydrolysis rate analysis in the nature of FIG. 7 to position an incoming biomass on the mathematical model and link the biomass to an analogous material having a similar hydrolysis rate. In this manner, it is possible to select an enzyme/prewash combination from available materials having the least cost, where the combination will attain, for example, an SSF process ethanol conversion of a predetermined amount over a predetermined time.

As to FIG. 8 in particular, the benefit of using a BSA prewash in an SSF process is shown for a particular corn stover specimen. When 25 FPU/g (FPU:CBU=1:1.75) cellulose hydrolyzing enzyme was added to a sample treated with lignin-blocking protein, the yield of ethanol increased approximately 5% after 24 hours, 10% after 48 hours, 20% after 72 hours, and 25% after 98 hours compared to a sample with the same enzyme loading that had not been treated with lignin-blocking protein.

Figure 9:
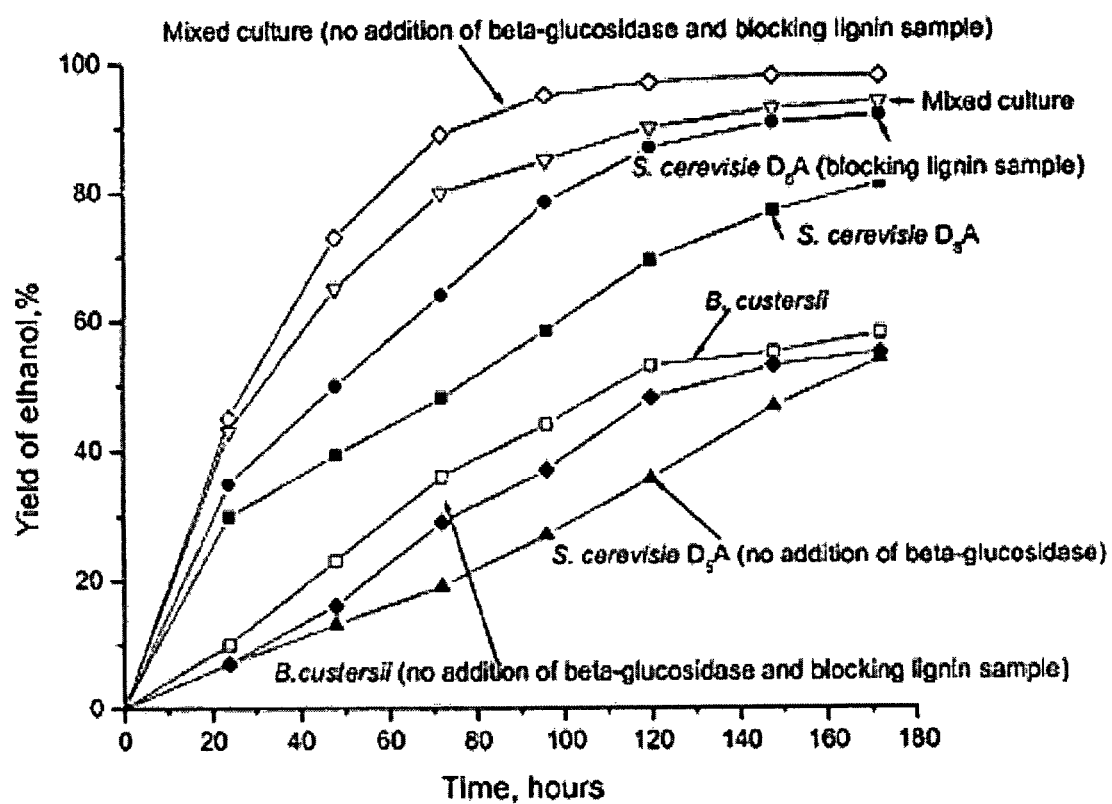
FIG. 9 shows comparison SSF results from *S. cerevisiae* D5A, *Brettanomyces custersii* and their mixed culture of pretreated corn stover with and without lignin-blocking treatment under 15 FPU/g cellulose loading

*Brettanomyces custersii* (CBS5512) is a promising glucose and cellulobiose fermentation yeast for SSF of cellulose for ethanol production because it can use cellobiose, a powerful inhibitor of cellulase action, directly (Spindler et al., Biotechnology Letters, 14 : 403-407, 1992). In particular, supplementation of β-glucosidase is more important for use of *S. cerevisiae* $D_5A$ than for *B. custersii* to get the same yields and rates of ethanol. Because lignin blocking treatment is particularly effective at reducing adsorption of β-glucosidase on lignin, less supplementation should be required when both a cellobiose fermenting yeast and lignin blocking are employed. For example our results show that a mixed culture of $D_5A$ and *B. custersii* in combination with lignin blocking gave better performance than use of any of these ingredients alone and also allowed elimination of supplementation with β-glucosidase. FIG. 9 shows comparison ethanol yield results using an SSF process comparing *S. cerevisiae* D5A, *Brettanomyces custersii* and their mixed culture, on pretreated corn stover with and without blocking-lignin treatment under 15 FPU/g cellulose loading (FPU:CBU=1:1.75). The use of lignin blocking peptide is shown to improve ethanol yield in mixed culture fermentation results, and in *S. cerevisiae* fermentation results—because the supplemented β-glucosidase is more available.

These results show that organisms which can ferment cellobiose and possibly other oligomers may be used in combination with lignin blocking compounds to reduce substantially the amount of enzyme required to convert pretreated cellulosic biomass into ethanol or other products. In particular, pretreated biomass is treated with a lignin blocking polypeptide to reduce non productive binding of cellulase to lignin and other non-cellulose fractions. Material treated with the lignin blocking polypeptide is added to a fermentation vessel along with cellulase enzyme and a fermentative organism, such as *Brettanomyces custersii*, that can convert cellobiose and possibly other cellulose oligomers directly to products in the simultaneous saccharification and fermentation (SSF) mode of operation. These ingredients can be added all at once or in some sequence, such as first the lignin blocking polypeptide, then cellulase, and finally the organism. In addition, the temperature may be tailored to capitalize on the sequence chosen, with one temperature being used when the lignin blocker is added, a high temperature when enzyme is added, and a lower temperature used before adding the fermentative organism, for the example sequence noted. The oligomer fermenting organism rapidly converts cellobiose, which is a powerful inhibitor of cellulase activity, to a fermentation product, thereby reducing the amount of cellobiose present together with the associated inhibitory effects. Furthermore, many lignin blocking polypeptides have been found to be particularly effective in substantially reducing nonproductive binding of the cellulase enzyme component, β-glucosidase, to lignin, resulting in more available β-glucosidase for converting cellobiose to glucose.

By using a lignin blocking polypeptide together with an oligomer fermenting organism, cellobiose concentrations are reduced, and so the effectiveness of the β-glucosidase enzyme is enhanced compared to either approach alone. This use of lignin blocking polypeptide results in better performance than is possible otherwise. Alternatively, this approach allows one to achieve the same performance with much less enzyme, substantially reducing costs. This approach may also be used to simultaneously ferment other biomass sugars into ethanol by adding the sugars from hemicellulose to the same vessel in the so-called simultaneous saccharification and cofermentation (SSCF) mode of operation, with the use of genetically engineered *Klebsiella oxytoca* and *E. coli* being examples of organisms that can ferment these sugars plus cellulose oligomers. The result of employing such organisms with a lignin blocking polypeptide makes it possible to achieve high rates, yields, and concentrations of products with much less enzyme and elimination of the associated high costs. Using a lignin blocking polypeptide in combination with a cellobiose fermenting organism can also advantageously reduce or eliminate the need to supplement with β-glucosidase.

EXAMPLE 8

SFS Processing

This example shows preferred process conditions for use in stop-flow-stop (SFS) processes, particularly, in the acidification that occurs in the solids holding tank 122 using additional acid 124, as illustrated in FIG. 1. The solids holding tank 122 may be a batch, flowthrough, or SFS reactor. SFS processing, as described herein, does not require the use of lignin-blocking polypeptides; however, it is also the case that SFS results are improved by the use of lignin-blocking polypeptides.

Corn stover grown near Harlan, Iowa was analyzed by the National Renewable Energy Laboratory, which provided a compositional analysis of glucan 36.1%, xylan 21.4%, arabinan 3.5%, mannan 1.8%, galactan 2.5%, lignin 17.2%, protein 4.0%, acetyl 3.2%, and ash 7.1%. A reactor made of 1 inch OD×10.7 mm tubing had an internal volume of 3.78 ml and was capable of holding about 6.5 g of the corn stover. The reactor was configured for flowthrough use by attaching stainless steel fittings (316 stainless steel, VCR fittings from Maine Valve and Fitting Co., of Bangor, Me.) and two stainless steel gasket filters with an average pore size of 5 μm at each end of the tubing to retain the corn stover. A heating coil was constructed of tubing to form a ¼ inch OD×0.035 inch ID heating coil. A cooling coil was constructed of tubing to form a ⅛ inch OD×0.028 inch ID cooling coil. The heating and cooling coils were experimentally determined to have sufficient length for incoming water to achieve a desired temperature before entering the reactor. The results of acid hydrolysis were measured as total sugars using post-hydrolysis fluids with 4 wt % sulfuric acid at 121° C. for one hour according to the method of Bouchard et al. (1991). Monomeric sugars were determined using a Bio-Rad Aminex HPX087P column on a Waters HPLC device equipped with a 2414 refractive index detector. A protein prewash was not used.

Acid hydrolysis was tested in the reactor using a dilute solution of sulfuric acid in water, i.e., 0.05 wt % sulfuric acid, at 180° C. The results of acid hydrolysis were measured as xylan removal under different flow conditions through the reactor. Flow conditions included 16 minutes of total residence time in the reactor. "Batch" flow was merely introducing the dilute acid solution into the reactor for combined residence with the corn stover. Two flowthrough runs were made, respectively, using 1 ml/min and 10 ml/min of the dilute acid solution. A stop-flow-stop run included flowing the dilute acid solution at 10 ml/min during an interval from 4 to 8 minutes, with batch conditions used for the remainder of the 16 minute residence time.

Figure 10:
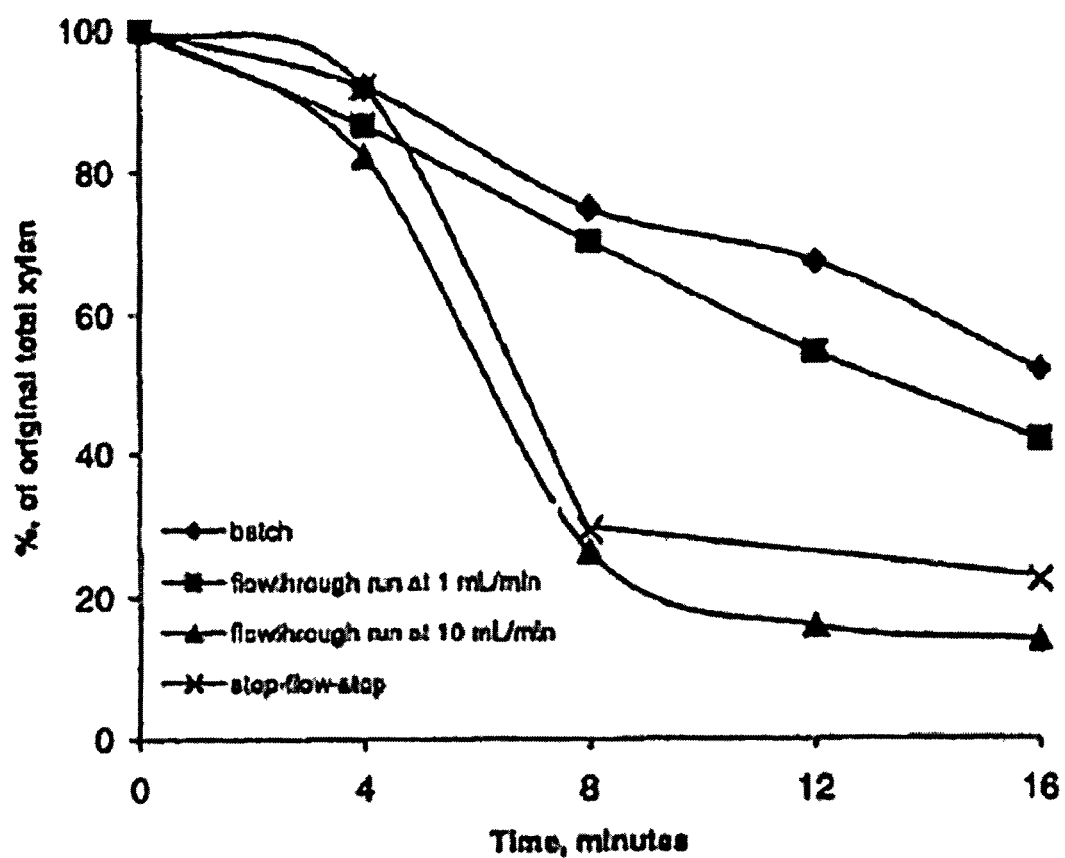
FIG. 10 shows a comparison of xylan hydrolysis over time under different flow conditions using a dilute acid solution.

FIG. 10 provides the results determined as a percentage of original xylan remaining in the reactor over the sixteen minute flow interval for the different flow conditions. Generally, xylose formation represents a hemicellulose sugar yield. Flowthrough operation enhanced xylan removal, as compared to batch conditions. Xylan removal increased with flow rate, for example, especially early in the reaction where the flow rate increased from 1 ml/min to 10 ml/min at 8 minutes total xylan removal also increased from about 25% to 75%. All flow conditions produced a relatively slow rate of hydrolysis out to approximately four minutes. This apparently is due to a delayed heat transfer through the biomass and limited interfacial area between the acid and biomass.

At the higher flow rates, the rate of xylan removal decreased once about 75% of the xylan was removed, for example, at about 8 minutes of flow for the SFS and 10 ml/min runs. This result is consistent with a concept that lignocellulosic materials have two categories: fast hydrolyzing and slow hydrolyzing. Approximately 30% of lignocellulosic materials are slow hydrolyzing. The high flow rate conditions are primarily effective in hydrolyzing the fast hydrolyzing lignocellulosic material, and less effective in hydrolyzing the slow hydrolyzing material.

The stop-flow-stop conditions have an advantage of reducing water consumption, together with associated energy demands, since the dilute acid solution flows for only a fraction of the total residence interval; however, hydrolysis efficiency is nearly as good as that obtainable from using the higher volume continuous 10 ml/min condition.

Table 4 provides a comparison of xylose concentrations for batch, flowthrough, and SFS acid pretreatment. "Batch 1" conditions were for 16 minutes as described above, while "Batch 2" were for 40 minutes. "FT1" and "FT2" were, respectively, the 1 ml/min and 10 ml/min runs described above. "SFS1" conditions included batch mode operation for 4 minutes followed by flow at 10 ml/min for 4 minutes and then batch mode for 8 minutes. "SFS2" conditions included batch mode for 4 minutes followed by flow at 10 ml/min for 8 minutes and then batch mode for 4 minutes.

TABLE 4

XYLOSE CONCENTRATIONS AND YIELDS FOR BATCH, SFS AND FLOWTHROUGH PRETREATMENT OF CORN STOVER WITH 0.05 WEIGHT PERCENT ACID AT 180° C.

| Operations | Xylose Monomer g/L | Xylose Oligomers g/L | Total Xylose | Total Xylose Yield % |
|---|---|---|---|---|
| Batch 1 | 0.026 | 0.856 | 0.882 | 34.4 |
| Batch 2 | 0.054 | 1.745 | 1.799 | 70.1 |
| FT1 | 0.082 | 1.550 | 1.632 | 63.6 |
| FT2 | 0.023 | 0.736 | 0.759 | 94.7 |
| SFS1 | 0.093 | 1.970 | 2.063 | 80.4 |
| SFS2 | 0.060 | 1/149 | 1.209 | 84.8 |

Table 4 shows that increased flow rates produce higher sugar yields, for example, where the yield increased from 64% to 95% between FT1 and FT2; however, the yield advantage is offset by relatively dilute concentrations. By way of comparison, the SFS1 flow conditions produced an intermediate total yield of 80.4%, but relatively high xylose concentrations. Alternatively, the dilute acid solution could be recycled for repeat passages through the corn stover to increase the xylose concentration.

Figure 11:
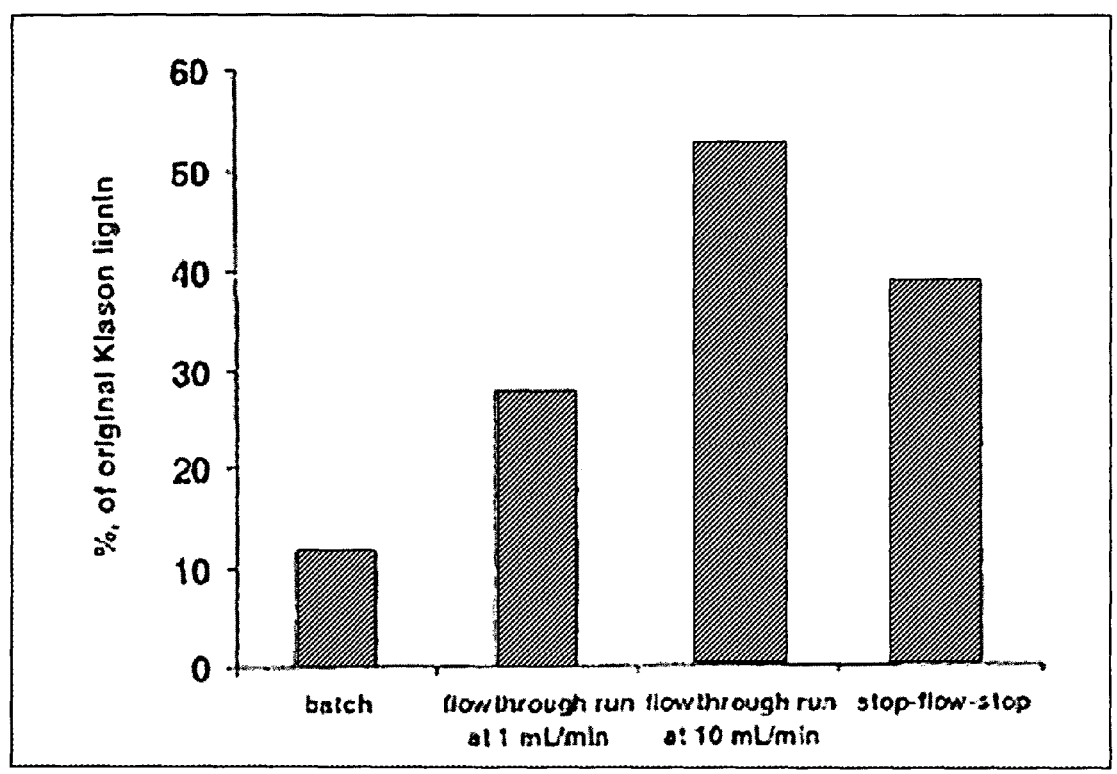
FIG. 11 shows a comparison lignin removal as caused by different flow conditions using a dilute acid solution.

The flow conditions were also observed to remove lignin from the corn stover. Before and after flow Klason lignin content was determined for each of the samples subjected to flow conditions as described in context of FIG. 10. FIG. 11 shows the results as a bar graph indicating the percentage of original Klason lignin removed from the sample after flow. Less than 12% of Klason lignin was removed by batch processing, whereas lignin removal increased to 28% with flowthrough at 1 ml/min and 52% with flowthrough at 10 ml/min. The SFS conditions resulted in 38% removal.

EXAMPLE 9

Pulp & Paper Process

The description above emphasizes protein treatment of cellulosic biomass in bioconversion processes; however, it is also the case that protein prewash and SFS processing are useful in other processes that use lignocellulosic materials, such as pulp manufacture, paper manufacture, and associated wastewater management processes.

Conventional pulp production includes, for example, the use of xylanase to facilitate or boost the bleaching of fibers. Xylanase reduces the need for bleaching chemicals, and has other advantages including economic and environmental benefits. Xylanase advantageously increases fiber brightness and increases production throughput in circumstances where the amount of bleaching chemical is limited. Use of xylanase reduces emissions of pollutants without requiring significant capital investment.

Figure 12:
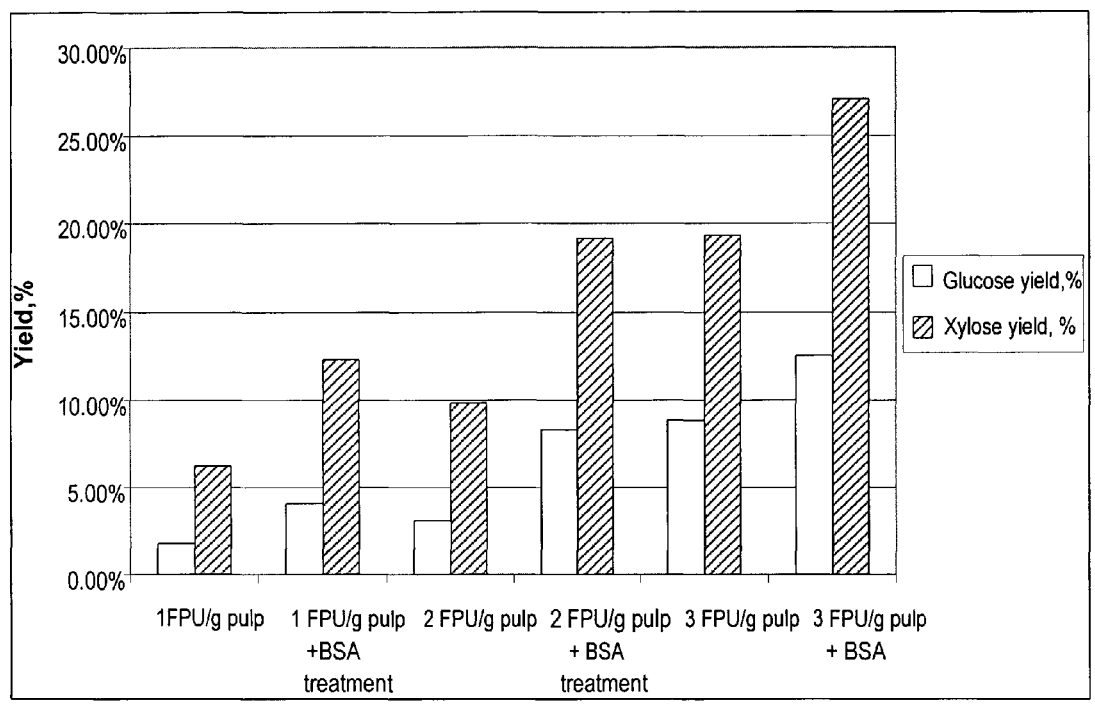
FIG. 12 shows lignin blocking treatments to enhance digestion of cellulose and xylan from unbleached pulp.

Xylanase binds with lignin in much the same way that cellulase and other hydrolyzing enzymes bind with lignin. Accordingly, the concept of using a protein prewash, as described above, also applies to processes using xylanase and other hydrolyzing enzymes on lignocellulosic substrates, even with an absence of cellulase. A xylanase solution for use in pulp and paper making processes may contain, for example, a lignin blocking polypeptide plus cellobiohydrolase from *Trichoderma reesei* and, optionally, a proteinase that will degrade the protein prewash after the cellobiohydrolase has had time to degrade the xylan. FIG. 12 shows the use of lignin blocking polypeptides (BSA) to increase, in unbleached pulp provided by Potlatch Corporation, Spokane, Wash., the digestion of cellulose and xylan under enzyme loading 2 FPU/g cellulose in respective amounts of about 45% and 48% over results in identical conditions run without the lignin blocking polypeptides.

In paper recycling operations, it is desirable to include a deinking process to reduce residual ink or dye and reduce the dirt count. A solution for use in deinking processes may include, for example, cellulase, xylanase, lipase and/or amylase. Table 5 discusses other problems that may be encountered in waste or recycled paper processing, together with categories of enzymatic treatments to resolve these problems.

TABLE 5

WASTE/RECYCLED PAPER PROBLEMS AND ENZYMATIC SOLUTIONS

| Problems | Enzyme treatments |
|---|---|
| Low brightness, cleanliness-- Caused by aging and heating of paper produced with bleached Kraft process pulp, e.g., due to uronic acid and/or hexenouronic acid affecting side groups on xylan | Cellulases/xylanase/peroxidase/ debranching enzymes |
| Poor strength | Cellulases/xylanases |
| High fines content | Celllulases |
| Heterologous composition | Cellulases/xylanases |
| Poor drainage | Cellulases |
| 'Sticky' materials-- Derived from resins, heat sensitive adhesives, hot melts, waxes, latex coatings, and binders from toner, ink, etc. | Cellulases |

Pulp and paper process effluents contain many contaminants including organic and inorganic material, bleaching chemicals, drainage aids, formation aids, defoaming aids, and biocides. These contaminants may be at least partially remediated using a combination of cellulase and lipase.

Mechanical pulp making processes may benefit from using cellulase and/or xylanase to increase dewatering, increase machine speed, increase wet web strength, and decrease refining energy. Hydrolyzing enzymes also provide reduced fiber coarseness with a corresponding decrease in handsheet roughness, and fiber strength loss. Kraft pulping processes similarly benefit, with an additional benefit in terms of increased handsheet density.

Each problem that is discussed above in context of having an enzymatic resolution is further remediated by using a protein prewash to bind lignin. As previously mentioned, the use of protein is effective to prevent binding between the hydrolyzing enzymes and the lignin, which enhances the availability of hydrolyzing enzyme.

EXAMPLE 10

Other Lignin Blocking Peptides

The lignin-blocking protein utilized in previous examples was BSA, which has a relatively high molecular weight of 66,000 Daltons. Other polypeptides and/or proteins that have the ability to block lignin binding are also useful. Thus, while proteins and/or polypeptides having an average molecular weight from 2,000 Daltons to 300,000 Daltons are generally useful, proteins or polypeptides having the capacity to block lignin binding, and having a molecular weight in the range of about 55,000 Daltons to about 80,000 Daltons are particularly useful. It has been confirmed by microscopic analysis of agricultural substrates including corn stover and wheat straw that fluorescently labeled peptides having molecular weights in this latter range are correctly sized to penetrate openings in the substrate in flow-through reactors while the peptides are also sufficiently large to enhance the lignin blocking effect. This ability to penetrate at 80,000 Daltons coupled with a larger peptide at 55,000 Daltons provides an optimum lignin blocking effect for the amount of peptide used.

Many proteins and polypeptides having a non-specific binding affinity for lignin may also be used to provide similar advantages. For example, such proteins as soybean protein, e.g., soybean flour and/or soybean meal may be used to block lignin by preparing the polypeptide or protein composition in water, and using the mixture as a biomass prewash. One benefit of using a lignin-blocking polypeptide is that a comparatively inexpensive polypeptide may be used to mitigate or eliminate the affinity which lignin would, otherwise, have for a more expensive enzyme. Enzymatic activity is not required of a lignin-blocking polypeptide, and a wide range of polypeptide materials are suitable for this purpose. By way of example, low cost proteinaceous waste materials may be used including fish or meat processing wastes, whey, grain processing wastes, sugar processing wastes, spoiled or expired food stocks, and/or algal proteins. Albumins are suitable proteins, especially, bovine serum albumin (BSA) and chicken egg albumin, but other polypeptides including soybean protein, amylase, and whey protein may provide effective alternatives at less overall expense.

Figure 6:
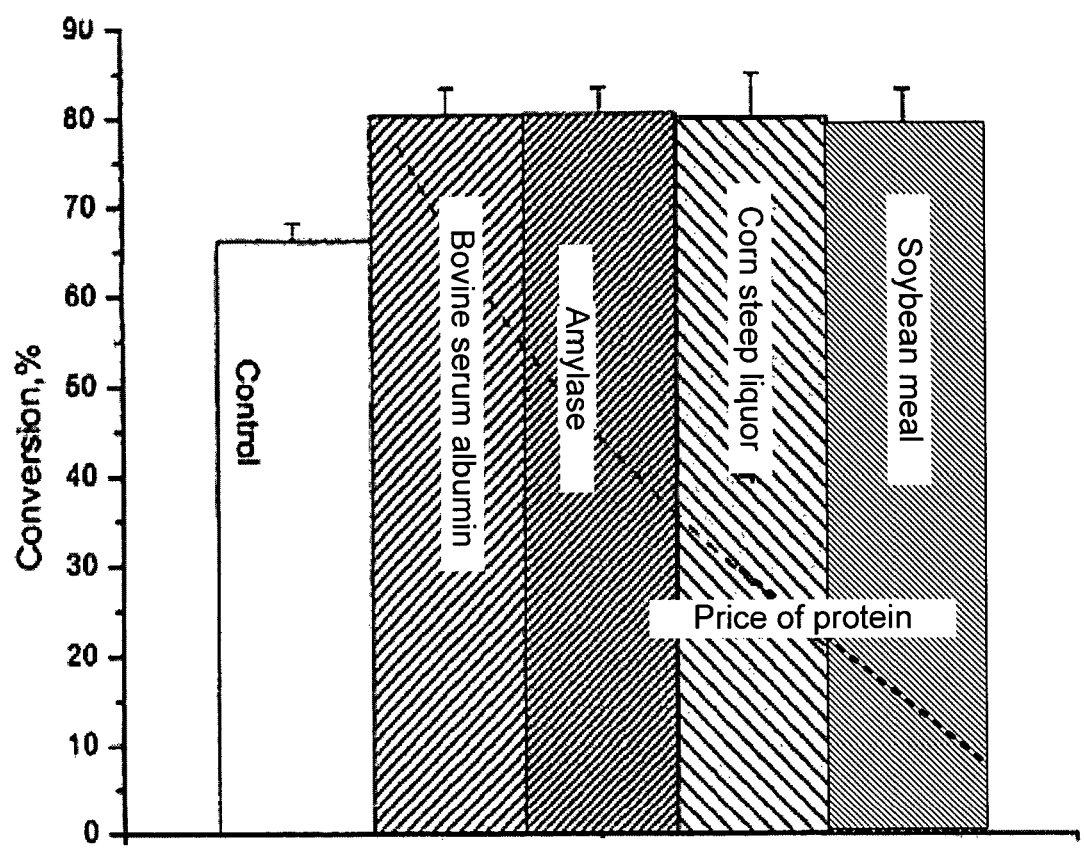
FIG. 6 shows the price of various lignin-blocking proteins compared to the percent conversion obtained from each protein.

A comparative study was done to determine the relative efficiency of various protein sources. Corn stover was pretreated with 1% by weight sulfuric acid (aq) at 140° C. for 40 minutes. A cellulose conversion efficiency was determined for specimens that were treated with lignin blocking proteins from various sources, namely, BSA, amylase, corn steep liquor and soybean meal, using cellulase having a concentration of 15 FPU/g cellulose for 72 hours. As shown in FIG. 6, all of the proteins provided approximately 80% conversion of cellulose from the pretreated corn stover. In contrast, a control consisting of pretreated corn stover that was not washed with a lignin blocking protein, produced only 65% conversion of the cellulose to sugar. FIG. 6 also shows that soybean meal is the cheapest source of protein, followed in order of increasing expense by corn steep liquor, amylase and bovine serum albumin. Since conversion efficiency is substantially insensitive to protein type the most cost effective protein may be selected; for example, where soybean meal is approximately eight times more cost effective than BSA.

Lignin-blocking/binding polypeptides and proteins, as defined for purposes herein, are molecules that interfere with the ability of lignin to bind cellulase or other cellulose-hydrolyzing enzymes. Furthermore, lignin-blocking/binding polypeptides and proteins have a high binding affinity for lignin and relatively insignificant binding activity (such as 1% to 3% w/w) for cellulose or cellulose hydrolyzing enzymes, such as cellulase. These lignin-blocking/binding proteins and polypeptides may be further described as having a size of 55,000 Daltons to 80,000 Daltons. However, smaller peptide fragments of BSA, or other lignin-blocking proteins, having a lower molecular weight, which retain sufficient lignin-binding activity, may also be used in a prewashing treatment composition.

The description of the specific embodiments reveal general concepts that others can modify and/or adapt for various applications or uses that do not depart from the general concepts. Therefore, such adaptations and modifications should and are intended to be comprehended within the meaning and range of equivalents of the disclosed embodiments. It is to be understood that the phraseology or terminology employed herein is for the purpose of description and not limitation.

What is claimed is:

1. A method for enhancing ethanol yield from a lignocellulosic biomass in a bioconversion process, said method comprising:
    treating said biomass, which comprises a lignin component and a cellulose component, with a composition containing a lignin-blocking proteinaceous material to provide a reaction mixture containing a treated lignin component,
    wherein the lignin-blocking proteinaceous material is selected from the group consisting of fish processing waste, meat processing waste, grain processing waste, sugar processing waste, spoiled or expired food stock, algal protein, soybean protein, whey protein, and combinations thereof;
    adding a hydrolyzing enzyme to the reaction mixture to hydrolyze the cellulose component of the biomass into carbohydrates;
    fermenting the carbohydrates in the reaction mixture in the presence of a sugar-to-ethanol converting microorganism; and
    extracting ethanol from the fermented reaction mixture.

2. The method of claim 1 wherein the hydrolyzing enzyme used in the step of adding comprises cellulase.

3. The method of claim 1 wherein the biomass used in the step of treating comprises at least 20% lignin by weight.

4. The method of claim 1 wherein the biomass used in the step of treating is further defined as comprising from 10% to 50% by weight lignin.

5. The method of claim 1 wherein the biomass used in the step of treating comprises at least 40% lignin by weight.

6. The method of claim 1 wherein the biomass used in the step of treating is selected from the group consisting of hardwood, softwood, herbaceous plants, grasses, and agricultural residues.

7. The method of claim 1, further comprising adding a cellobiose fermenting organism to the biomass.

8. The method of claim 1 wherein the lignin-blocking proteinaceous material used in the step of treating further comprises bovine serum albumin (BSA).

9. A method for enhancing ethanol yield from a lignocellulosic biomass in a bioconversion process, comprising:
    treating said biomass, which comprises a lignin component and a cellulose component, with a composition containing a lignin-blocking proteinaceous material to provide a reaction mixture containing a treated lignin component,
    wherein the lignin-blocking proteinaceous material includes two or more proteinaceous materials selected from the group consisting of fish processing waste, meat processing waste, grain processing waste, sugar processing waste, spoiled or expired food stock, algal protein, albumin, soybean protein and whey protein;
    adding a hydrolyzing enzyme to the reaction mixture to hydrolyze the cellulose component of the biomass into carbohydrates;
    fermenting the carbohydrates in the reaction mixture in the presence of a sugar-to-ethanol converting microorganism; and
    extracting ethanol from the fermented reaction mixture.

10. The method of claim 9 wherein the hydrolyzing enzyme used in the step of adding comprises cellulase.

11. The method of claim 9 wherein the biomass used in the step of treating comprises at least 20% lignin by weight.

12. The method of claim 9 wherein the biomass used in the step of treating is further defined as comprising from 10% to 50% by weight lignin.

13. The method of claim 9 wherein the biomass used in the step of treating comprises at least 40% lignin by weight.

14. The method of claim 9 wherein the biomass used in the step of treating is selected from the group consisting of hardwood, softwood, herbaceous plants, grasses, and agricultural residues.

15. The method of claim 9, further comprising adding a cellobiose fermenting organism to the biomass.

16. The method of claim 9 wherein the step of treating is performed before the step of adding.

17. The method of claim 16, further comprising a subsequent step of treating the biomass with a composition including a lignin-blocking proteinaceous material, the subsequent step being performed after the step of adding the hydrolyzing enzyme.

18. A method for enhancing ethanol yield from a lignocellulosic biomass in a bioconversion process, comprising:

treating said biomass, which comprises a lignin component and a cellulose component, with a composition containing a lignin-blocking proteinaceous material to provide a reaction mixture containing a treated lignin component, wherein the lignin-blocking proteinaceous material includes bovine serum albumin (BSA) and one or more proteinaceous materials selected from the group consisting of fish processing waste, meat processing waste, grain processing waste, sugar processing waste, spoiled or expired food stock, algal protein, chicken egg albumin, soybean protein and whey protein;

adding a hydrolyzing enzyme to the reaction mixture to hydrolyze the cellulose component of the biomass into carbohydrates;

fermenting the carbohydrates in the reaction mixture in the presence of a sugar-to-ethanol converting microorganism; and extracting ethanol from the fermented reaction mixture.

19. The method of claim 18, further comprising adding a cellobiose fermenting organism to the biomass.

20. The method of claim 18 wherein the step of treating is performed before the step of adding.

21. The method of claim 20, further comprising a subsequent step of treating the biomass with a composition including a lignin-blocking proteinaceous material, the subsequent step being performed after the step of adding the hydrolyzing enzyme.

* * * * *